US012565536B2

(12) United States Patent
Brinkmann et al.

(10) Patent No.: US 12,565,536 B2
(45) Date of Patent: Mar. 3, 2026

(54) METHOD FOR GENERATING AVID-BINDING MULTISPECIFIC ANTIBODIES

(71) Applicant: Hoffmann-La Roche Inc., Little Falls, NJ (US)

(72) Inventors: Ulrich Brinkmann, Weilheim (DE); Alexander Bujotzek, Munich (DE); Guy Georges, Habach (DE); Anja Schrade, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 1020 days.

(21) Appl. No.: 17/488,698

(22) Filed: Sep. 29, 2021

(65) Prior Publication Data

US 2022/0098326 A1    Mar. 31, 2022

Related U.S. Application Data

(63) Continuation of application No. PCT/EP2020/058271, filed on Mar. 25, 2020.

(30) Foreign Application Priority Data

Mar. 29, 2019    (EP) .................................... 19166038

(51) Int. Cl.
C07K 16/32          (2006.01)
C07K 16/28          (2006.01)

(52) U.S. Cl.
CPC .......... *C07K 16/32* (2013.01); *C07K 16/2863* (2013.01); *C07K 16/2896* (2013.01); *C07K 2317/31* (2013.01); *C07K 2317/92* (2013.01)

(58) Field of Classification Search
CPC .......... C07K 2317/31; C07K 2317/565; C07K 16/00

See application file for complete search history.

(56) References Cited

U.S. PATENT DOCUMENTS

2010/0004431 A1    1/2010  Bernett et al.
2010/0261620 A1    10/2010  Almagro et al.

FOREIGN PATENT DOCUMENTS

WO    2017/023761 A1    2/2017
WO    2018/093866 A1    5/2018
WO    2018/182422 A1    10/2018

OTHER PUBLICATIONS

Kirik, U., et al., "Antibody Heavy Chain Variable Domains of Different Germline Gene Origins Diversity through Different Paths". 2017. Front. Immunol, 8:1433. (Year: 2017).*

Willis, J. R., et al., "Human Germline Antibody Gene Segments Encode Polyspecific Antibodies". 2013. PLoS Comput Biol 9(4): e1003045. (Year: 2013).*
Yu, S., et al., A novel asymmetrical anti-HER2/CD3 bispecific antibody exhibits potent cytotoxicity for HER2-positive tumor cells, Journal Experimental & Clinical Cancer Research (2019) 38:355, https://doi.org/10.1186/s13046-019-1354-1 (Year: 2019).*
Sela-Culang, I., et al., "The structural basis of antibody-antigen recognition", Frontiers in Immunology, published: Oct. 8, 2013, doi: 10.3389/fimmu.2013.00302 (Year: 2013).*
Bostrom, J., et al., "Improving Antibody Binding Affinity and Specificity for Therapeutic Development", 2009, Therapeutic Antibodies: Methods and Protocols, vol. 25, Humana Press, pp. 353-376 (Year: 2009).*
Haidar, et al., "Backbone Flexibility of CDR3 and Immune Recognition of Antigens", J Mol Biol, 2014, 426:1583-1599 (Year: 2014).*
Ho, M., et al., "In Vitro Antibody Evolution Targeting Germline Hot Spots to Increase Activity of an Anti-CD22 Immunotoxin" J Biol Chem 280(1):607-617 (Jan. 7, 2005).
"International Preliminary Report on Patentability—PCT/EP2020/058271" (Report Issuance Date: Jun. 17, 2021; Chapter II), :pp. 1-8 (Jun. 17, 2021).
"International Search Report—PCT/EP2020/058271" (w/Written Opinion), :pp. 1-14 (Jun. 12, 2020).
Mazor, Y., et al., "Enhanced tumor-targeting selectivity by modulating bispecific antibody binding affinity and format valence" Sci Rep 7:(40098) 1-11 (Jan. 9, 2017).
Mazor, Y., et al., "Insights into the molecular basis of a bispecific antibody's target selectivity" MABS 7(3):461-469 (Mar. 2, 2015).
Schrade, A., et al., "Back-to-Germline (B2G) Procedure for Antibody Devolution" Antibodies 8(3):(45) 1-19 (Aug. 26, 2019).
Slaga et al., "Avidity-based binding to HER2 results in selective killing of HER2-overexpressing cells by anti-HER2/CD3" Sci. Transl. Med. 10, eaat5775:pp. 1-11 (Oct. 17, 2018).

(Continued)

*Primary Examiner* — Brad Duffy
(74) *Attorney, Agent, or Firm* — Hoffmann-La Roche Inc.

(57) ABSTRACT

Herein is reported a method for increasing the (avid-) binding specificity of a bispecific antibody comprising a first mammalian or mammalianized binding site specifically binding to a first (cell-surface) antigen and a second binding site specifically binding to a second (cell-surface) antigen, wherein the first mammalian or mammalianized binding site is at least a pair of an immunoglobulin light chain variable domain and immunoglobulin heavy chain variable domain, by decreasing the binding affinity of the mammalian or mammalianized binding site to its antigen by mutating in the first mammalian or mammalianized binding site at least one amino acid residue at a position in the CDRs of the light chain variable domain or in the CDR1 or CDR2 of the heavy chain variable domain or in the two framework positions directly preceding the CDR3 in the heavy chain variable domain to an amino acid residue present at said position in a germline immunoglobulin amino acid sequence of the same mammalian species as that of the mammalian or mammalianized binding site.

7 Claims, 26 Drawing Sheets

(56)  References Cited

OTHER PUBLICATIONS

Zha et al., "An unexpected protective role of low-affinity allergen-specific IgG through the inhibitory receptor FcγRIIb" J Allergy Clin Immunol (EPUB: Jan. 31, 2018), 142(5):pp. 1529-1536.e6 (Nov. 2018).

* cited by examiner

Figure 1

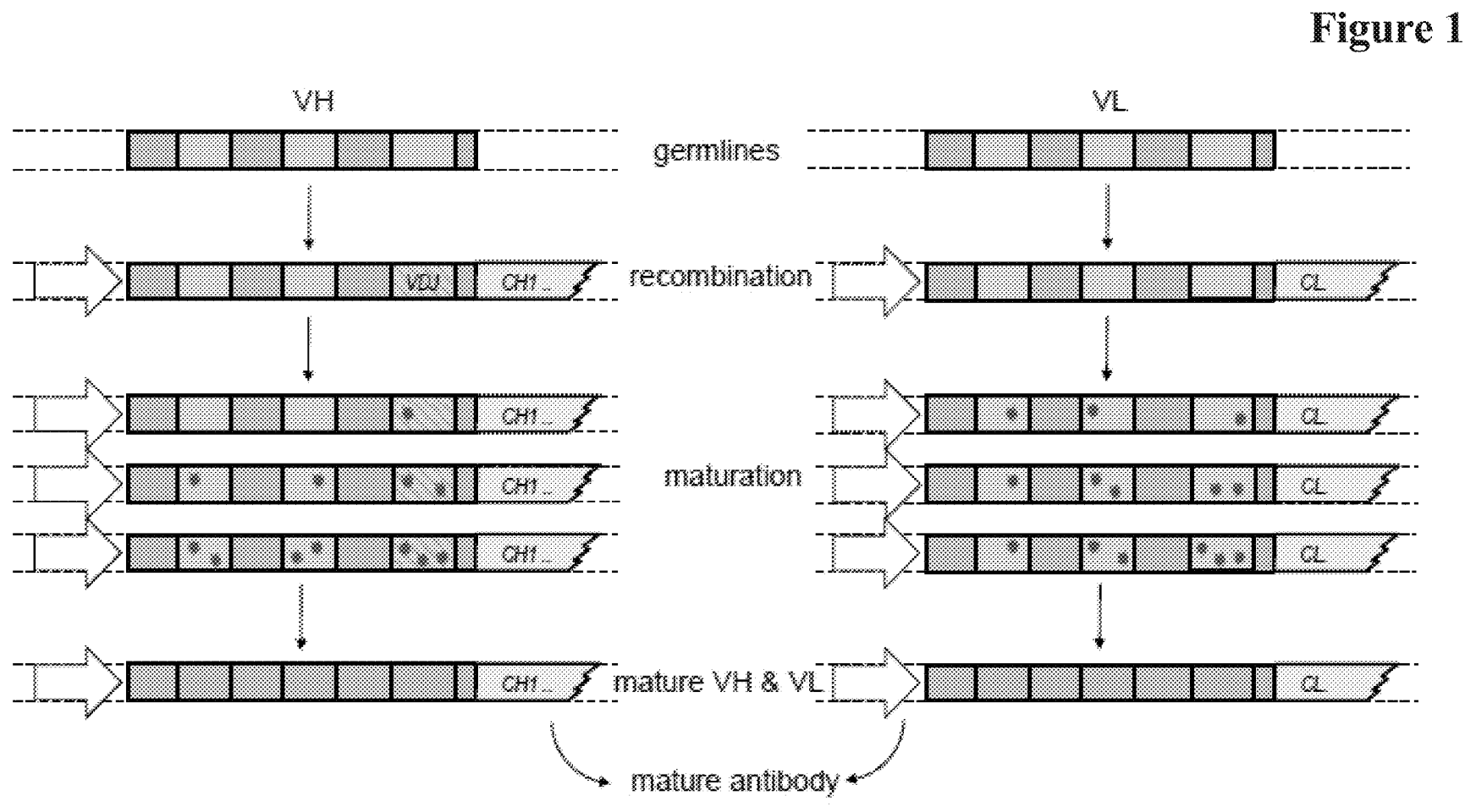

- - - $K_D$ Hw ~ Lw (parent IgG)

METHOD FOR GENERATING AVID-BINDING MULTISPECIFIC ANTIBODIES

CROSS REFERENCE TO RELATED APPLICATIONS

This application is a continuation of International Application No. PCT/EP2020/058271, filed Mar. 25, 2020, which claims benefit to European Patent Application No. 19166038.0, filed Mar. 29, 2019, all of which are hereby expressly incorporated by reference in their entirety as though fully set forth herein.

The current invention is in the field of antibody technology, more specifically in the field multispecific antibodies and variants thereof generated by amino acid sequence modification. Herein is reported a method for the generation of multispecific antibodies with avid binding properties starting from monospecific affine-binding antibodies.

BACKGROUND

Combination therapy of two monoclonal antibodies (mAbs) have shown promising results, e.g. in the treatment of solid tumors. However, the administration of two mAbs requires individual regulatory review and approval. The next generation of antibody therapeutics, therefore, include bispecific antibodies (bsAbs) featuring the ability to bind two targets at a time (Tiller and Tessier 2015; Brinkmann and Kontermann 2017; Garber 2014; Haurum 2006). There are various scenarios how these bsAbs can improve therapeutic activity: One is the ability to target specific immune cells or proteins in addition to the therapeutic target and, thus, enhancing effector function or antibody delivery to a specific organ, respectively (van Spriel, van Ojik, and van De Winkel 2000; Niewoehner et al. 2014; Fesnak et al. 2016). Other ways to improve antibody efficacy through bispecificity are the blocking of two different biological pathways or simply increasing the specificity towards tumor cells by dual targeting of two individual cell surface antigens (Kontermann 2012).

Is an antigen not exclusively displayed on target cells, but also on non-pathogenic cells, it is desirable to design an antibody that targets also a second antigen, which in combination with the first one is only found at the intended site of therapy or action. In this case, although preferential, bispecificity itself does not necessarily come with increased specificity. If monovalent affinity of the bsAb is sufficient for binding, cells that express only one antigen can still be bound. To achieve increased specificity by bispecificity and to avoid off-target effects, avid-binding is required. In such a setting monovalent binding affinity is not sufficient to retain the antibody on the cell surface and only if at least two binding sites can bind to their specific antigens the bsAbs is retained on the cell surface. Thus, such binders recognize a target antigen with high specificity yet with very low monovalent affinity.

Current approaches to generate low affinity binding entities include, e.g., de-novo generation of antibodies or introduction of mutations to decrease affinities of existing antibodies. De-novo generation of antibodies with very low (in ideal cases non-detectable) affinity in monovalent format proves to be difficult and incompatible with standard antibody generation technologies, which require significant binding for hit detection. To circumvent this problem and nevertheless generate avid-binding entities, one approach is to take existing specific binders and introduce mutations into the binding region to reduce affinity. Therefore, their structure is determined, antigen interactions are modelled and disturbing mutations are introduced. As of today, alanine scanning mutagenesis is the method of choice to explore protein-protein interfacial residues (Mazor et al. 2017; Pons, Rajpal, and Kirsch 1999). The disadvantage of these approaches is either that the crystal structure of the antibody-antigen complex needs to be known or determined first, that the introduction of mutations without the knowledge of structure might disturb antibody structure dramatically, and that the alanine mutations introduce polyreactivity (Chuang et al. 2015). Computational calculations of alanine replacement of charged amino acids, including arginine, aspartic acid, glutamic acid, lysine, and histidine often results in disagreement with values obtained from laboratory experiments (Kollman et al. 2000; Wang et al. 2001).

WO 2018/093866 reported anti-MET antibodies, bispecific antigen binding molecules that bind met, and methods of use thereof. Mazor, Y., et al., reported enhanced tumor-targeting selectivity by modulating bispecific antibody binding affinity and format valence (Sci. Rep. 7 (2017) 40098). Ho, M., et al., reported in vitro antibody evolution targeting germ line hot spots to increase activity of an anti-CD22 immunotoxin (J. Biol. Chem. 280 (2004) 607-617). Thus, there is the need for a generalizable approach to generate antibody derivatives with reduced affinity in the absence of polyreactivity.

SUMMARY OF THE INVENTION

Bispecific antibodies (bsAbs) with avidity-enhanced specificity can be used to address target cells with very high specificity. Such avid-binding bsAbs shall bind efficiently only to cells that express the two antigens of the bsAb, yet not to cells that express only one of those. To build such bsAbs, combinations of binders are required that recognize the two antigens with high specificity yet with various (incl. very low monovalent) affinities. This is especially suitable when the two antigens are on the same cell.

The current invention is based, at least in part, on the finding that antibodies with high specificity can be converted into variant antibodies that retain binding-specificity but have reduced monovalent binding-affinity. Such variant antibodies, more precisely the binding site(s) thereof, can be used as binding sites in an avid-binding multispecific antibody with avidity-enhanced specificity.

One aspect of the invention is a method for increasing the (avid-)binding specificity/avid binding/decreasing the binding affinity of a multispecific antibody comprising a first binding site specifically binding to a first (cell-surface) antigen and a second binding site specifically binding to a second (cell-surface) antigen, wherein at least said first binding site is a mammalian or mammalianized binding site, wherein the first binding site is at least a pair of an immunoglobulin light chain variable domain and an immunoglobulin heavy chain variable domain, (wherein the increasing the (avid-)binding specificity/avid binding/decreasing the binding affinity is) by decreasing the binding affinity of the first binding site to its antigen by mutating in the first binding site at at least one position the amino acid residue to an amino acid residue present at said position in a germline immunoglobulin amino acid sequence of the same mammalian species as the species of the first binding site and thereby increasing the (avid-)binding specificity/avid binding of the bispecific antibody comprising a first binding site specifically binding to a first (cell-surface) antigen and a second binding site specifically binding to a second (cell-surface) antigen.

The term "avid-binding specificity/avid binding" as used herein denotes the binding specificity/binding of a molecule towards one or more cells based on the combined strength of the interactions of the multiple binding sites of the single, i.e. one, molecule (antibody) with their respective target(s) (specific antigen(s)).

The term "germline immunoglobulin amino acid sequence" as used herein denotes the amino acid sequence encoded by a germline gene, which is in vivo serving as starting sequence during antibody maturation in B-cells (see FIG. 1) without any somatic mutations.

One aspect of the invention is a method for increasing the total binding avidity of a multispecific antibody comprising a first binding site specifically binding to a first (cell-surface) antigen and a second binding site specifically binding to a second (cell-surface) antigen, wherein at least said first binding site is a mammalian or mammalianized binding site, wherein the first binding site is at least a pair of an immunoglobulin light chain variable domain and an immunoglobulin heavy chain variable domain, by decreasing the binding affinity of the first binding site to its antigen by mutating in the first binding site at at least one position the amino acid residue to an amino acid residue present at said position in a germline immunoglobulin amino acid sequence of the same mammalian species as the species of the first binding site and thereby increasing the total binding avidity of the bispecific antibody comprising a first binding site specifically binding to a first (cell-surface) antigen and a second binding site specifically binding to a second (cell-surface) antigen.

In one embodiment of all aspects the multispecific antibody is at least a bispecific antibody. In a preferred embodiment the multispecific antibody is a bispecific antibody.

In one embodiment of all aspects the first cell-surface antigen and the second cell-surface antigen are on the same cell.

In one embodiment of all aspects the at least one mutated amino acid residue is i) at a position in the CDRs of the light chain variable domain, and/or ii) at a position in CDR1 or CDR2 of the heavy chain variable domain, and/or iii) in the two framework positions directly preceding the CDR3 in the heavy chain variable domain.

In one embodiment of all aspects the CDRs are determined according to Kabat.

In one embodiment of all aspects the germline immunoglobulin amino acid sequence is that germline immunoglobulin amino acid sequence that has the highest percent identity in a (BLASTp) alignment of all germline immunoglobulin amino acid sequences of said mammalian species. BLASTp is available at https://blast.ncbi.nlm.nih.gov/Blast.cgi?PAGE=Proteins.

In one embodiment of all aspects only the sequence fragment encompassing the first residue of CDR1 of the heavy chain variable domain to the last residue of the CDR2 of the heavy chain variable domain is taken into account/ used for the determination of the germline immunoglobulin amino acid sequence in case of the heavy chain variable domain.

In one embodiment of all aspects the sidechain of the amino acid residue to be mutated is solvent accessible (i.e. not completely buried).

A buried amino acid residue is not accessible to solvent molecules. Thus, the terms "not completely buried" and "solvent accessible", which can be used interchangeably herein, denote amino acid residues that can interact with a solute molecule by electrostatic interactions, hydrogen bond interactions, Van-der-Waals interactions, or hydrophobic interactions.

In one embodiment of all aspects the sidechain of the amino acid residue to be mutated is not involved in a VH-VL interaction.

In one embodiment of all aspects the sidechain of the amino acid residue to be mutated is involved in at least one interaction with the antigen.

Interactions between residues or surfaces or structures (i.e. amino acid-amino acid-interactions or VH-VL interactions) in Fvs are interactions between residues or surfaces or structures of Fv's that provide contact to and retention on/of antigens; these interactions can be electrostatic interactions, hydrogen bond interactions, Van-der-Waals interactions, hydrophobic interactions and others.

In one embodiment of all aspects the mutated first-binding site has the same or a reduced polyreactivity as the non-mutated first binding site. In one embodiment of all aspects the mutated first binding site, i.e. the binding site with decreased affinity, is free of polyreactivity. In one embodiment the polyreactivity is determined by surface plasmon resonance or an immunoassay.

The term "free of polyreactivity" as used herein denotes that a binding site (of an antibody) cannot bind to multiple non-related antigens due to non-specific interactions or high flexibility in the binding site or due to simple non-specific stickiness.

In one embodiment of all aspects the second binding site is a second pair of an immunoglobulin light chain variable domain an immunoglobulin heavy chain variable domain, the second binding site is a mammalian or mammalianized binding site, and the mutating is of at least one amino acid residue in the first and the second binding site.

In one embodiment of all aspects the mammal is a human.

In one embodiment of all aspects the first and/or the second pair of an immunoglobulin light chain variable domain an immunoglobulin heavy chain variable domain is a pair of a human or humanized immunoglobulin light chain variable domain and a human or humanized immunoglobulin heavy chain variable domain.

In one embodiment of all aspects the method is for increasing the (avid-)binding specificity/avid binding by reducing the monovalent binding affinity/binding affinity of at least one binding site of the multispecific antibody.

One aspect of the invention is a multispecific antibody obtained with a method according to the invention.

One aspect of the invention is an isolated nucleic acid encoding a multispecific antibody obtained with a method according to the invention.

One aspect of the invention is an isolated cell comprising the nucleic acid according to the invention.

In one embodiment of all aspects the cell is a CHO, HEK, Sp2/0, PER.C6 or BHK cell.

One aspect of the invention is a method for producing a multispecific antibody comprising the following steps:

cultivating the cell according to the invention so that the antibody is produced, and recovering the multispecific antibody from the cell or the cultivation medium, optionally purifying the multispecific antibody with one or more chromatography steps.

All permutation of aspects and embodiments mentioned herein are likewise disclosed without being explicitly described.

DETAILED DESCRIPTION OF EMBODIMENTS OF THE INVENTION

Bispecific antibodies (bsAbs) with avidity-enhanced specificity can be used to target cells with very high specificity. Such avid-binding bsAbs shall bind efficiently only to cells that express the two antigens of the bsAb, yet not to cells that express only one of those. To build such avid-binding bsAbs combinations of binders are required that recognize the two antigens with high specificity yet with various (especially very low monovalent) affinities. The method according to the invention provides a means for producing binders that are suitable for forming part of an avid-binding bsAb.

The current invention is based, at least in part, on the finding that (parent) antibodies with high specificity can be converted into derivatives that retain binding specificity but have reduced monovalent binding affinity with likewise increased binding affinity. It has been found that mutations to be introduced into antibody CDR regions to reduce binding affinity without influencing binding specificity can be identified without requiring any structure of an antibody-antigen complex.

The current invention is based, at least in part, on the finding that by reverting the B-cell maturation or mammalianization process, in which the affinity of antibodies is increased, especially with preference on CDR residues with high antigen contact probability, antibodies can be obtained/generated that recognize their respective antigen with maintained high specificity but yet with (very) low monovalent affinity. This is achieved by placing germline encoded amino acid residues at those CDR residues/positions with high antigen contact probability, which have been changed during the somatic affinity maturation or mammalianization process in vivo/in silico. Thereby VH and VL domains and Fv-combinations are produced/generated/obtained that retain their specificity but are 'de-matured' to different degrees. The de-maturation process according to the method of the current invention affects on- and off-rates, and can produce binding sites with extremely low affinity for which, for example, antigen binding can only be detected in bivalent formats.

It has been found that compared with methods based on alanine replacement in CDRs to identify residues for mutation (so far the most frequently applied technology) the method according to the current invention is more reliable/predictable, e.g. without introduction of non-specific stickiness or polyreactivity.

Definitions

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991). The amino acid positions of all constant regions and domains of the heavy and light chain can be numbered according to the Kabat numbering system described in Kabat, et al., Sequences of Proteins of Immunological Interest, 5th ed., Public Health Service, National Institutes of Health, Bethesda, MD (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, MD (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein.

It is also to be noted that the terms "comprising", "including", and "having" can be used interchangeably.

To a person skilled in the art procedures and methods are well known to convert an amino acid sequence, e.g. of a peptidic linker or fusion polypeptide, into a corresponding encoding nucleic acid sequence. Therefore, a nucleic acid is characterized by its nucleic acid sequence consisting of individual nucleotides and likewise by the amino acid sequence of a peptidic linker or fusion polypeptide encoded thereby.

The use of recombinant DNA technology enables the generation derivatives of a nucleic acid. Such derivatives can, for example, be modified in individual or several nucleotide positions by substitution, alteration, exchange, deletion or insertion. The modification or derivatization can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA; Hames, B. D., and Higgins, S. G., Nucleic acid hybridization—a practical approach (1985) IRL Press, Oxford, England).

Useful methods and techniques for carrying out the current invention are described in e.g. Ausubel, F. M. (ed.), Current Protocols in Molecular Biology, Volumes I to III (1997); Glover, N. D., and Hames, B. D., ed., DNA Cloning: A Practical Approach, Volumes I and II (1985), Oxford University Press; Freshney, R. I. (ed.), Animal Cell Culture—a practical approach, IRL Press Limited (1986); Watson, J. D., et al., Recombinant DNA, Second Edition, CHSL Press (1992); Winnacker, E. L., From Genes to Clones; N.Y., VCH Publishers (1987); Celis, J., ed., Cell Biology, Second Edition, Academic Press (1998); Freshney, R. I., Culture of Animal Cells: A Manual of Basic Technique, second edition, Alan R. Liss, Inc., N.Y. (1987).

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

The term "antibody" herein is used in the broadest sense and encompasses various antibody structures, including but not limited to monoclonal antibodies, multispecific antibodies (e.g. bispecific antibodies, trispecific antibodies), and antibody fragments so long as they exhibit the desired antigen-binding activity.

An antibody in general comprises two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The constant domains of an antibody heavy chain comprise the CH1-domain, the CH2-domain and the CH3-domain, whereas the light chain comprises only one constant domain, CL, which can be of the kappa isotype or the lambda isotype.

The variable domain of an immunoglobulin's light or heavy chain in turn comprises different segments, i.e. four framework regions (FR) and three hypervariable regions (HVR).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "binding (to an antigen)" denotes the binding of an antibody to its antigen in an in vitro assay, in one embodiment in a binding assay in which the antibody is bound to a surface and binding of the antigen to the antibody is measured by Surface Plasmon Resonance (SPR). Binding means the measurement of the binding capacity of e.g. the antibody for target A or target B, or for a capture molecule e.g. anti-human-Fab-capture for the antibody.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al.

The term "valent" as used within the current application denotes the presence of a specified number of binding sites in a (antibody) molecule. As such, the terms "bivalent", "tetravalent", and "hexavalent" denote the presence of two binding site, four binding sites, and six binding sites, respectively, in a (antibody) molecule. The bispecific antibodies as reported herein are in one preferred embodiment "bivalent".

The term "binding affinity" denotes the strength of the interaction of a single binding site with its respective target. Experimentally, the affinity can be determined e.g. by measuring the kinetic constants for association (kA) and dissociation (kD) of the antibody and the antigen in the equilibrium.

The term "binding avidity" denotes the combined strength of the interaction of multiple binding sites of one molecule (antibody) with the same target. As such, avidity is the combined synergistic strength of bond affinities rather than the sum of bonds. Requisites for avidity are: polyvalency of a molecule, such as an antibody, or of a functional multimer to one target (antigen), —multiple accessible epitopes on one soluble target OR multiple binding of an antibody to one epitope each on various immobilized targets.

The complex association does not differ between affine and avid binding. However, the complex dissociation for avid binding depends on the simultaneous dissociation of all binding sites involved. Therefore, the increase of binding strength due to avid binding (compared to affine binding) depends on the dissociation kinetics/complex stability: the bigger (higher) the complex stability, the less likely is the simultaneous dissociation of all involved binding sites; for very stable complexes, the difference of affine vs. avid binding becomes essentially zero; —the smaller (lower) the complex stability, the more likely is the simultaneous dissociation of all involved binding sites; the difference of affine vs. avid binding is increased.

Wolfguy Numbering Scheme

The Wolfguy numbering defines CDR regions as the set union of the Kabat and Chothia definition. Furthermore, the numbering scheme annotates CDR loop tips based on CDR length (and partly based on sequence) so that the index of a CDR position indicates if a CDR residue is part of the ascending or the descending loop. A comparison with established numbering schemes is shown in the following Table.

TABLE

Numbering of CDR-L3 and CDR-H3 using Chothia/Rabat (Ch-Rb), Honegger and Wolfguy numbering schemes. The latter has increasing numbers from the N-terminal basis to the CDR peak and decreasing ones starting from the C-terminal CDR end. Rabat schemes fix the two last CDR residues and introduce letters to accommodate for the CDR length. In contrast to Rabat nomenclature, the Honegger numbering does not use letters and is common for VH and VL.

| Wolfguy VH | Ch-Kb | Honegger | Ch-Kb | Wolfguy VL |
|---|---|---|---|---|
| 326 | 88 | 102 | 84 | 730 |
| 327 | 89 | 103 | 85 | 731 |
| 328 | 90 | 104 | 86 | 732 |
| 329 | 91 | 105 | 87 | 733 |
| 330 | 92 | C | 88 | 734 |
| 331 | 93 | 107 | 89 | 751 |
| 332 | 94 | 108 | 90 | 752 |
| 351 | 95 | 109 | 91 | 753 |
| 352 | 96 | 110 | 92 | 754 |
| 353 | 97 | 111 | 93 | 755 |
| 354 | 98 | 112 | 94 | 756 |
| 355 | 99 | 113 | 95 | 757 |
| 356 | 100 | 114 | 95a | 758 |
| 357 | 100a | 115 | 95b | 759 |
| 358 | 100b | 116 | 95c | 760 |
| 359 | 100c | 117 | 95d | 761 |
| 360 | 100d | 118 | 95e | 762 |
| 361 | 100e | 119 | 95f | 763 |
| 362 | 100f | 120 | | 764 |
| 363 | 100g | 121 | | 765 |
| 364 | 100h | 122 | | 766 |
| 384 | 100i | 123 | | 784 |
| 385 | 100j | 124 | | 785 |
| 386 | 100k | 125 | | 786 |
| 387 | 100l | 126 | | 787 |
| 388 | | 127 | | 788 |
| 389 | | 128 | | 789 |
| 390 | | 129 | | 790 |
| 391 | | 130 | | 791 |
| 392 | | 131 | | 792 |
| 393 | | 132 | | 793 |
| 394 | | 133 | | 794 |
| 395 | | 134 | | 795 |
| 396 | | 135 | | 796 |
| 397 | | 136 | | 797 |
| 398 | 101 | 137 | 96 | 798 |
| 399 | 102 | 138 | 97 | 799 |
| 401 | 103 | F W | 98 | 801 |
| 402 | 104 | 140 | 99 | 802 |
| 403 | 105 | 141 | 100 | 803 |
| 404 | 106 | 142 | 101 | 804 |

Wolfguy is designed such that structurally equivalent residues (i.e. residues that are very similar in terms of conserved spatial localization in the Fv structure) are numbered with equivalent indices as far as possible.

An example for a Wolfguy-numbered full-length VH and VL sequence can be found in the Table below.

Table: VH (left) and VL (right) sequence of the crystal structure with PDB ID 3PP4 (21), numbered with Wolfguy, Kabat and Chothia. In Wolfguy, CDR-H1-H3, CDR-L2 and CDR-L3 are numbered depending only on length, while CDR-L1 is numbered depending on loop length and canonical cluster membership. The latter is determined by calculating sequence similarities to different consensus sequences. Here, we only give a single example of CDR-L1 numbering.

TABLE

VH (left) and VL (right) sequence of the crystal structure with PDB ID 3PP4 (21), numbered with Wolfguy, Kabat and Chothia. In Wolfguv, CDR-H1-H3, CDR-L2 and CDR-L3 are numbered depending only on length, while CDR-L1 is numbered depending on loop length and canonical cluster membership. The latter is determined by calculating sequence similarities to different consensus sequences. Here, we only give a single example of CDR-L1 numbering.

| | PDB ID 3PP4 VH | | | | | |
|---|---|---|---|---|---|---|
| | Wolfguy | | Kabat | | Chothia | |
| Framework 1 | 101 | Q | 1 | Q | 1 | Q |
| | 102 | V | 2 | V | 2 | V |
| | 103 | Q | 3 | Q | 3 | Q |
| | 104 | L | 4 | L | 4 | L |
| | 105 | V | 5 | V | 5 | V |
| | 106 | Q | 6 | Q | 6 | Q |
| | 107 | S | 7 | S | 7 | S |
| | 108 | G | 8 | G | 8 | G |
| | 109 | A | 9 | A | 9 | A |
| | 110 | E | 10 | E | 10 | E |
| | 111 | V | 11 | V | 11 | V |
| | 112 | K | 12 | K | 12 | K |
| | 113 | K | 13 | K | 13 | K |
| | 114 | P | 14 | P | 14 | P |
| | 115 | G | 15 | G | 15 | G |
| | 116 | S | 16 | S | 16 | S |
| | 117 | S | 17 | S | 17 | S |
| | 118 | V | 18 | V | 18 | V |
| | 119 | K | 19 | K | 19 | K |
| | 120 | V | 20 | V | 20 | V |
| | 121 | S | 21 | S | 21 | S |
| | 122 | C | 22 | C | 22 | C |
| | 123 | K | 23 | K | 23 | K |
| | 124 | A | 24 | A | 24 | A |
| | 125 | S | 25 | S | 25 | S |
| CDR-H1 | 151 | G | 26 | G | 26 | G |
| | 152 | Y | 27 | Y | 27 | Y |
| | 153 | A | 28 | A | 28 | A |
| | 154 | F | 29 | F | 29 | F |
| | 155 | S | 30 | S | 30 | S |
| | 156 | Y | 31 | Y | 31 | Y |
| | 157 | . | 32 | S | 31a | S |
| | 158 | . | 33 | W | 31b | . |
| | 193 | . | 34 | I | 31c | . |
| | 194 | . | 35 | N | 31d | . |
| | 195 | . | 35a | . | 31e | . |
| | 196 | S | 35b | . | 32 | S |
| | 197 | W | 35c | . | 33 | W |
| | 198 | I | 35d | . | 34 | I |
| | 199 | N | 35e | . | 35 | N |
| Framework 2 | 201 | W | 36 | W | 36 | W |
| | 202 | V | 37 | V | 37 | V |
| | 203 | R | 38 | R | 38 | R |
| | 204 | Q | 39 | Q | 39 | Q |
| | 205 | A | 40 | A | 40 | A |
| | 206 | P | 41 | P | 41 | P |
| | 207 | G | 42 | G | 42 | G |
| | 208 | Q | 43 | Q | 43 | Q |
| | 209 | G | 44 | G | 44 | G |

TABLE-continued

VH (left) and VL (right) sequence of the crystal structure
with PDB ID 3PP4 (21), numbered with Wolfguy, Kabat and
Chothia. In Wolfguy, CDR-H1-H3, CDR-L2 and CDR-L3 are
numbered depending only on length, while CDR-L1 is numbered
depending on loop length and canonical cluster membership.
The latter is determined by calculating sequence similarities
to different consensus sequences. Here, we only give a
single example of CDR-L1 numbering.

| Region | Wolfguy | | Kabat | | Chothia | |
|---|---|---|---|---|---|---|
| | 210 | L | 45 | L | 45 | L |
| | 211 | E | 46 | E | 46 | E |
| | 212 | W | 47 | W | 47 | W |
| | 213 | M | 48 | M | 48 | M |
| | 214 | G | 49 | G | 49 | G |
| CDR-H2 | 251 | R | 50 | R | 50 | R |
| | 252 | I | 51 | I | 51 | I |
| | 253 | F | 52 | F | 52 | F |
| | 254 | P | 52a | P | 52a | P |
| | 255 | G | 52b | . | 52b | . |
| | 256 | . | 52c | . | 52c | . |
| | 286 | . | 52d | . | 52d | . |
| | 287 | . | 53 | G | 53 | G |
| | 288 | D | 54 | D | 54 | D |
| | 289 | G | 55 | G | 55 | G |
| | 290 | D | 56 | D | 56 | D |
| | 291 | T | 57 | T | 57 | T |
| | 292 | D | 58 | D | 58 | D |
| | 293 | Y | 59 | Y | 59 | Y |
| | 294 | N | 60 | N | 60 | N |
| | 295 | G | 61 | G | 61 | G |
| | 296 | K | 62 | K | 62 | K |
| | 297 | F | 63 | F | 63 | F |
| | 298 | K | 64 | K | 64 | K |
| | 299 | G | 65 | G | 65 | G |
| Framework 3 | 301 | R | 66 | R | 66 | R |
| | 302 | V | 67 | V | 67 | V |
| | 303 | T | 68 | T | 68 | T |
| | 304 | I | 69 | I | 69 | I |
| | 305 | T | 70 | T | 70 | T |
| | 306 | A | 71 | A | 71 | A |
| | 307 | D | 72 | D | 72 | D |
| | 308 | K | 73 | K | 73 | K |
| | 309 | S | 74 | S | 74 | S |
| | 310 | T | 75 | T | 75 | T |
| | 311 | S | 76 | S | 76 | S |
| | 312 | T | 77 | T | 77 | T |
| | 313 | A | 78 | A | 78 | A |
| | 314 | Y | 79 | Y | 79 | Y |
| | 315 | M | 80 | M | 80 | M |
| | 316 | E | 81 | E | 81 | E |
| | 317 | L | 82 | L | 82 | L |
| | 318 | S | 82a | S | 82a | S |
| | 319 | S | 82b | S | 82b | S |
| | 320 | L | 82c | L | 82c | L |
| | 321 | R | 83 | R | 83 | R |
| | 322 | S | 84 | S | 84 | S |
| | 323 | E | 85 | E | 85 | E |
| | 324 | D | 86 | D | 86 | D |
| | 325 | T | 87 | T | 87 | T |
| | 326 | A | 88 | A | 88 | A |
| | 327 | V | 89 | V | 89 | V |
| | 328 | Y | 90 | Y | 90 | Y |
| | 329 | Y | 91 | Y | 91 | Y |
| | 330 | C | 92 | C | 92 | C |
| | 331 | A | 93 | A | 93 | A |
| | 332 | R | 94 | R | 94 | R |
| CDR-H3 | 351 | N | 95 | N | 95 | N |
| | 352 | V | 96 | V | 96 | V |
| | 353 | F | 97 | F | 97 | F |
| | 354 | D | 98 | D | 98 | D |
| | 355 | G | 99 | G | 99 | G |
| | 356 | . | 100 | Y | 100 | Y |
| | 357 | . | 100a | W | 100a | W |
| | 358 | . | 100b | L | 100b | L |
| | 359 | . | 100c | . | 100c | . |
| | 360 | . | 100d | . | 100d | . |
| | 361 | . | 100e | . | 100e | . |
| | 362 | . | 100f | . | 100f | . |
| | 363 | . | 100g | . | 100g | . |
| | 364 | . | 100h | . | 100h | . |
| | 365 | . | 100i | . | 100i | . |
| | 385 | . | 100j | . | * | . |
| | 386 | . | 100k | . | * | . |
| | 387 | . | 100l | . | * | . |
| | 388 | . | 100m | . | * | . |
| | 389 | . | 100n | . | * | . |
| | 390 | . | 100o | . | * | . |
| | 391 | . | 100p | . | * | . |
| | 392 | . | 100q | . | * | . |
| | 393 | . | 100r | . | * | . |
| | 394 | . | 100s | . | * | . |
| | 395 | Y | 100t | . | * | . |
| | 396 | W | 100u | . | * | . |
| | 397 | L | 100v | . | * | . |
| | 398 | V | 101 | V | 101 | V |
| | 399 | Y | 102 | Y | 102 | Y |
| Framework 4 | 401 | W | 103 | W | 103 | W |
| | 402 | G | 104 | G | 104 | G |
| | 403 | Q | 105 | Q | 105 | Q |
| | 404 | G | 106 | G | 106 | G |
| | 405 | T | 107 | T | 107 | T |
| | 406 | L | 108 | L | 108 | L |
| | 407 | V | 109 | V | 109 | V |
| | 408 | T | 110 | T | 110 | T |
| | 409 | V | 111 | V | 111 | V |
| | 410 | S | 112 | S | 112 | S |
| | 411 | S | 113 | S | 113 | S |

PDB ID 3PP4 VL

| Region | Wolfguy | | Kabat | | | |
|---|---|---|---|---|---|---|
| Framework 1 | 501 | D | 1 | D | 1 | D |
| | 502 | I | 2 | I | 2 | I |
| | 503 | V | 3 | V | 3 | V |
| | 504 | M | 4 | M | 4 | M |
| | 505 | T | 5 | T | 5 | T |
| | 506 | Q | 6 | Q | 6 | Q |
| | 507 | T | 7 | T | 7 | T |
| | 508 | P | 8 | P | 8 | P |
| | 509 | L | 9 | L | 9 | L |
| | 510 | S | 10 | S | 10 | S |
| | 511 | L | 11 | L | 11 | L |
| | 512 | P | 12 | P | 12 | P |
| | 513 | V | 13 | V | 13 | V |
| | 514 | T | 14 | T | 14 | T |
| | 515 | P | 15 | P | 15 | P |
| | 516 | G | 16 | G | 16 | G |
| | 517 | E | 17 | E | 17 | E |
| | 518 | P | 18 | P | 18 | P |
| | 519 | A | 19 | A | 19 | A |
| | 520 | S | 20 | S | 20 | S |
| | 521 | I | 21 | I | 21 | I |
| | 522 | S | 22 | S | 22 | S |
| | 523 | C | 23 | C | 23 | C |
| CDR-L1 | 551 | R | 24 | R | 24 | R |
| | 552 | S | 25 | S | 25 | S |
| | 553 | S | 26 | S | 26 | S |
| | 556 | K | 27 | K | 27 | K |
| | 561 | S | 27a | S | 28 | S |
| | 562 | L | 27b | L | 29 | L |
| | 563 | L | 27c | L | 30 | L |
| | 581 | H | 27d | H | 30a | H |
| | 582 | S | 27e | S | 30b | S |
| | 583 | N | 28 | N | 30c | N |
| | 594 | G | 29 | G | 30d | G |
| | 595 | I | 30 | I | 30e | I |
| | 596 | T | 31 | T | 31 | T |
| | 597 | Y | 32 | Y | 32 | Y |
| | 598 | L | 33 | L | 33 | L |
| | 599 | Y | 34 | Y | 34 | Y |

| | | | | | | |
|---|---|---|---|---|---|---|

13

TABLE-continued

VH (left) and VL (right) sequence of the crystal structure with PDB ID 3PP4 (21), numbered with Wolfguy, Kabat and Chothia. In Wolfguv, CDR-H1-H3, CDR-L2 and CDR-L3 are numbered depending only on length, while CDR-L1 is numbered depending on loop length and canonical cluster membership. The latter is determined by calculating sequence similarities to different consensus sequences. Here, we only give a single example of CDR-L1 numbering.

| | | | | | | |
|---|---|---|---|---|---|---|
| Framework 2 | 601 | W | 35 | W | 35 | W |
| | 602 | Y | 36 | Y | 36 | Y |
| | 603 | L | 37 | L | 37 | L |
| | 604 | Q | 38 | Q | 38 | Q |
| | 605 | K | 39 | K | 39 | K |
| | 606 | P | 40 | P | 40 | P |
| | 607 | G | 41 | G | 41 | G |
| | 608 | Q | 42 | Q | 42 | Q |
| | 609 | S | 43 | S | 43 | S |
| | 610 | P | 44 | P | 44 | P |
| | 611 | Q | 45 | Q | 45 | Q |
| | 612 | L | 46 | L | 46 | L |
| | 613 | L | 47 | L | 47 | L |
| | 614 | I | 48 | I | 48 | I |
| | 615 | Y | 49 | Y | 49 | Y |
| CDR-L2 | 651 | Q | 50 | Q | 50 | Q |
| | 652 | . | * | . | * | . |
| | 653 | . | * | . | * | . |
| | 692 | . | * | . | * | . |
| | 693 | . | * | . | * | . |
| | 694 | M | 51 | M | 51 | M |
| | 695 | S | 52 | S | 52 | S |
| | 696 | N | 53 | N | 53 | N |
| | 697 | L | 54 | L | 54 | L |
| | 698 | V | 55 | V | 55 | V |
| | 699 | S | 56 | S | 56 | S |
| Framework 3 | 701 | G | 57 | G | 57 | G |
| | 702 | V | 58 | V | 58 | V |
| | 703 | P | 59 | P | 59 | P |
| | 704 | D | 60 | D | 60 | D |
| | 705 | R | 61 | R | 61 | R |
| | 706 | F | 62 | F | 62 | F |
| | 707 | S | 63 | S | 63 | S |
| | 708 | G | 64 | G | 64 | G |
| | 709 | S | 65 | S | 65 | S |
| | 710 | G | 66 | G | 66 | G |
| | 711 | S | 67 | S | 67 | S |
| | 712 | G | 68 | G | 68 | G |
| | 713 | . | * | . | * | . |
| | 714 | . | * | . | * | . |
| | 715 | T | 69 | T | 69 | T |
| | 716 | D | 70 | D | 70 | D |
| | 717 | F | 71 | F | 71 | F |
| | 718 | T | 72 | T | 72 | T |
| | 719 | L | 73 | L | 73 | L |
| | 720 | K | 74 | K | 74 | K |
| | 721 | I | 75 | I | 75 | I |
| | 722 | S | 76 | S | 76 | S |
| | 723 | R | 77 | R | 77 | R |
| | 724 | V | 78 | V | 78 | V |
| | 725 | E | 79 | E | 79 | E |
| | 726 | A | 80 | A | 80 | A |
| | 727 | E | 81 | E | 81 | E |
| | 728 | D | 82 | D | 82 | D |
| | 729 | V | 83 | V | 83 | V |
| | 730 | G | 84 | G | 84 | G |
| | 731 | V | 85 | V | 85 | V |
| | 732 | Y | 86 | Y | 86 | Y |
| | 733 | Y | 87 | Y | 87 | Y |
| | 734 | C | 88 | C | 88 | C |
| CDR-L3 | 751 | A | 89 | A | 89 | A |
| | 752 | Q | 90 | Q | 90 | Q |
| | 753 | N | 91 | N | 91 | N |
| | 754 | L | 92 | L | 92 | L |
| | 755 | E | 93 | E | 93 | E |
| | 756 | . | 94 | L | 94 | L |
| | 757 | . | 95 | P | 95 | P |
| | 758 | . | 95a | . | 95a | . |
| | 793 | . | 95b | . | 95b | . |
| | 794 | . | 95c | . | 95c | . |
| | 795 | . | 95d | . | 95d | . |

14

TABLE-continued

VH (left) and VL (right) sequence of the crystal structure with PDB ID 3PP4 (21), numbered with Wolfguy, Kabat and Chothia. In Wolfguv, CDR-H1-H3, CDR-L2 and CDR-L3 are numbered depending only on length, while CDR-L1 is numbered depending on loop length and canonical cluster membership. The latter is determined by calculating sequence similarities to different consensus sequences. Here, we only give a single example of CDR-L1 numbering.

| | | | | | | |
|---|---|---|---|---|---|---|
| | 796 | L | 95e | . | 95e | . |
| | 797 | P | 95f | . | 95f | . |
| | 798 | Y | 96 | Y | 96 | Y |
| | 799 | T | 97 | T | 97 | T |
| Framework 4 | 801 | F | 98 | F | 98 | F |
| | 802 | G | 99 | G | 99 | G |
| | 803 | G | 100 | G | 100 | G |
| | 804 | G | 101 | G | 101 | G |
| | 805 | T | 102 | T | 102 | T |
| | 806 | K | 103 | K | 103 | K |
| | 807 | V | 104 | V | 104 | V |
| | 808 | E | 105 | E | 105 | E |
| | 809 | I | 106 | I | 106 | I |
| | 810 | K | 107/106 | K | 107 | K |

Multispecific Antibodies

In certain embodiments, the antibody is a multispecific antibody, e.g. at least a bispecific antibody. Multispecific antibodies are monoclonal antibodies that have binding specificities for at least two different antigens or epitopes. In certain embodiments, one of the binding specificities is for a first antigen and the other is for a different second antigen. In certain embodiments, multispecific antibodies may bind to two different epitopes of the same antigen. Multispecific antibodies may also be used to localize cytotoxic agents to cells, which express the antigen. Multispecific antibodies can be prepared as full-length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M., et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P., et al., Proc. Natl. Acad. Sci. USA 90 (1993) 6444-6448); and using single-chain Fv (scFv) dimers (see, e.g., Gruber, M., et al., J. Immunol. 152 (1994) 5368-5374); and preparing trispecific antibodies as described, e.g., in Tutt, A., et al., J. Immunol. 147 (1991) 60-69).

The antibody or fragment can also be a multispecific antibody as described in WO 2009/080251, WO 2009/080252, WO 2009/080253, WO 2009/080254, WO 2010/112193, WO 2010/115589, WO 2010/136172, WO 2010/145792, or WO 2010/145793.

The antibody or fragment thereof may also be a multispecific antibody as disclosed in WO 2012/163520.

Bispecific antibodies are generally antibody molecules that specifically bind to two different, non-overlapping epitopes on the same antigen or to two epitopes on different antigens.

Different bispecific antibody formats are known.

Exemplary bispecific antibody formats for which the methods as reported herein can be used are IgG-type antibody with domain exchange: a multispecific IgG antibody comprising a first Fab fragment and a second Fab fragment, wherein in the first Fab fragment a) only the CH1 and CL domains are replaced by each other (i.e. the light chain of the first Fab fragment comprises a VL and a CH1 domain and the heavy chain of the first Fab fragment comprises a VH and a CL domain);

b) only the VH and VL domains are replaced by each other (i.e. the light chain of the first Fab fragment comprises a VH and a CL domain and the heavy chain of the first Fab fragment comprises a VL and a CH1 domain); or c) the CH1 and CL domains are replaced by each other and the VH and VL domains are replaced by each other (i.e. the light chain of the first Fab fragment comprises a VH and a CH1 domain and the heavy chain of the first Fab fragment comprises a VL and a CL domain); and wherein the second Fab fragment comprises a light chain comprising a VL and a CL domain, and a heavy chain comprising a VH and a CH1 domain;

the IgG-type antibody with domain exchange may comprises a first heavy chain including a CH3 domain and a second heavy chain including a CH3 domain, wherein both CH3 domains are engineered in a complementary manner by respective amino acid substitutions, in order to support heterodimerization of the first heavy chain and the modified second heavy chain, e.g. as disclosed in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, or WO 2013/096291 (incorporated herein by reference);

the one-armed single chain format (=one-armed single chain antibody): antibody comprising a first binding site that specifically binds to a first epitope or antigen and a second binding site that specifically binds to a second epitope or antigen, whereby the individual chains are as follows light chain (variable light chain domain+light chain kappa constant domain)

combined light/heavy chain (variable light chain domain+light chain constant domain+peptidic linker+variable heavy chain domain+CH1+Hinge+CH2+CH3 with knob mutation)

heavy chain (variable heavy chain domain+CH1+Hinge+CH2+CH3 with hole mutation);

the two-armed single chain format (=two-armed single chain antibody): antibody comprising a first binding site that specifically binds to a first epitope or antigen and a second binding site that specifically binds to a second epitope or antigen, whereby the individual chains are as follows combined light/heavy chain 1 (variable light chain domain+light chain constant domain+peptidic linker+variable heavy chain domain+CH1+Hinge+CH2+CH3 with hole mutation)

combined light/heavy chain 2 (variable light chain domain+light chain constant domain+peptidic linker+variable heavy chain domain+CH1+Hinge+CH2+CH3 with knob mutation);

the common light chain bispecific format (=common light chain bispecific antibody): antibody comprising a first binding site that specifically binds to a first epitope or antigen and a second binding site that specifically binds to a second epitope or antigen, whereby the individual chains are as follows light chain (variable light chain domain+light chain constant domain)

heavy chain 1 (variable heavy chain domain+CH1+Hinge+CH2+CH3 with hole mutation)

heavy chain 2 (variable heavy chain domain+CH1+Hinge+CH2+CH3 with knob mutation);

a dual targeting Fab: antibody comprising two (non-overlapping) paratopes in a complementary pair of a VH and a VL domain, wherein the first paratope comprises (consists of) amino acid residues from CDR1 and CDR3 of the VL domain and CDR2 of the VH domain, and the second paratope comprises (consists of) residues from CDR1 and CDR3 of the VH domain and CDR2 of the VL domain.

The term "non-overlapping" in this context indicates that an amino acid residue that is comprised within the first paratope of the DutaFab is not comprised in the second paratope, and an amino acid that is comprised within the second paratope of the DutaFab is not comprised in the first paratope.

In one embodiment the bispecific antibody is a IgG-type antibody with domain exchange.

In one embodiment the bispecific antibody is a one-armed single chain antibody.

In one embodiment the bispecific antibody is a two-armed single chain antibody.

In one embodiment the bispecific antibody is a common light chain bispecific antibody.

In one embodiment the bispecific antibody is a dual targeting Fab.

Compositions and Methods

A set of antibody derivatives is generated by nature during the generation and maturation of antibodies in B-cells (MacLennan 1994) (see FIG. 1). During the 1st step recombination generates binder specific for a specific antigen, yet relatively low affinity. VDJ recombination generates initial H3 on a defined VH germline, combined with one defined VL. Multiple rounds of somatic mutations lead to an increased antibody affinity with selective pressure towards antigen binding in the germinal center. These maturation steps generate variations in antigen binding region, better binder selection and lead to the evolution of the antibody. The affinity of the resulting mature antibody towards its antigen is increased by many orders of magnitude when compared to corresponding naïve B-cell receptors and its structure differs from germline-encoded counterparts (Chan and Brink 2012).

The invention is based, at least in part, on the finding that by identifying affinity-modulating back-mutations for a given animal- or human-derived VH or VL sequence it is possible to "reverse" the antibody maturation process in B-cell (see FIG. 1). Thus, the method according to the current invention cannot be applied to antibodies generated from in-vitro library panning/selection approaches of (synthetic) libraries.

The method according to the current invention generates a set of antibody derivatives with reduced affinity but retaining specificity by reversing B-cell maturation (FIG. 2) or mammalianization. It has been found that with the method according to the current invention antibody derivatives with functionalities of antibodies of different stages of the maturation tree can be generated. These have different affinities, yet retaining the specificity of the matured starting antibody.

The method according to the current invention comprises up to five subsequent steps, preferably three subsequent steps, whereof the first two are mandatory and the third one is optional (see FIG. 2).

1) Identification of the Germlines from which the Mature/Matured Antibody Might be Derived The VH and VL germlines from which the antibody might have descended are identified by performing a sequence alignment, e.g. using BLASTp (Altschul et al. 1990) search, against a database of IGHV and IGKV/IGLV germline sequences, e.g. that of the IMGT (Brochet, Lefranc, and Giudicelli 2008; Giudicelli, Brochet, and Lefranc 2011). The germline sequence with the highest percent identity is assumed to be the germline of origin. Due to the complexities of VDJ recombination in combination with the occurrence of additional mutations in the process of maturation, it is not possible to determine the definitive non-matured (VDJ only) protein sequence of CDR-H3.

The search can be narrowed down by specifying the species of origin of the antibody.

In cases where the input sequences belong to a humanized antibody and the species of origin is unknown the procedure can be modified by querying the database with the sequence segment ranging from the begin of CDR-H1 to the end of CDR-H2 only.

Framework and CDR regions can be assigned with the software ANARCI (Dunbar and Deane 2016) using the WolfGuy antibody numbering scheme (Bujotzek, Dunbar, et al. 2015).

After the most likely germline sequence(s) has (have) been identified, it is (they are) aligned to the input sequence based on their WolfGuy numbering. Every mismatch between input and germline sequence represents a possible maturation event, and, thus, a potential candidate for a back-mutation.

2) Selection of the Back-Mutations

The back-mutations are selected with the following criteria are applied:

i) the amino acid is different with respect to the germline (s) identified in step 1) and is situated in the CDR regions or in the framework positions directly preceding CDR-H3 (WolfGuy 331 and 332), whereby the final positions of CDR-H2 (WolfGuy 295 to 299) are excluded;

ii) the amino acid sidechain is not to be completely buried, i.e. it is located in/at the interface between the domains; 'buried' residues or sequence stretches or entities or surfaces are not accessible to solvent molecules;

iii) the amino acid sidechain is not to be involved in VH-VL interactions; VL and VH domains of antibodies form VL-VH pairs, which are present as functional Fv's with antigen binding properties; VH-VL interactions are residues, sequences, stretches or surfaces which come into contact upon meeting VH and VL as Fv heterodimer;

iv) there are known antibody-antigen complex structures (e.g. in the PDB (Berman et al, 2000)) where the amino acid sidechain at this position is involved in chemical interactions with the antigen.

Thereby mutations with a high probably of being involved in antigen binding are identified.

The structural read-out necessary for criteria ii) and iii) in one embodiment can be extracted from a homology model of the variable region of the antibody. A homology model in the context of the invention denotes an atomic-resolution model of the variable region of interest (defined by the input sequences of VH and VL), constructed from available experimentally derived antibody crystal structures of similar sequence that are being used as structural templates. Such a model can be generated with any modelling software, such as e.g. MoFvAb (Bujotzek, Fuchs, et al. 2015).

The statistics about antibody-antigen contacts used for iv) is in one embodiment be extracted, e.g., from a set antibody complex structures retrieved from SAbDab (Dunbar et al. 2014), made non-redundant with regard to the CDR sequences of the antibodies involved, and having been subdivided by antigen type into "protein" and "peptide", to reflect that protein- and peptide-binding antibodies exhibit a different profile of preferential paratope residues.

Exemplary sets of statistical antibody-antigen contacts for antibody-peptide and antibody-protein interactions is provided in the following Tables. All not presented residues/positions have a value of 0 in each of columns 3, 4, 6 and 7.

| | | antibody-antigen contacts for antigen type 'peptide' | | | | |
|---|---|---|---|---|---|---|
| 1: WolfGuy* Index | 2: region | 3: average amino acid sidechain solvent accessibility change [%] | 4: average number of chemical interactions with antigen | 5: number of samples | 6: number of samples with change of solvent accessible surface | 7: number of samples with chemical interactions with antigen |
| 101 | VH-Framework-1 | 0.15 | 0 | 158 | 2 | 0 |
| 102 | | 0.53 | 0.02 | 194 | 7 | 4 |
| 124 | | 0.01 | 0 | 205 | 1 | 0 |
| 152 | CDR-H1 | 0.7 | 0.03 | 204 | 12 | 5 |
| 153 | | 1.45 | 0.03 | 205 | 19 | 5 |
| 154 | | 0.03 | 0 | 205 | 1 | 0 |
| 155 | | 1.3 | 0.02 | 205 | 19 | 5 |
| 156 | | 9.62 | 0.16 | 205 | 84 | 24 |
| 157 | | 1.63 | 0 | 13 | 2 | 0 |
| 195 | | 17.88 | 0.39 | 31 | 17 | 7 |
| 196 | | 5.74 | 0.24 | 205 | 77 | 36 |
| 197 | | 23.34 | 1.1 | 205 | 169 | 110 |
| 199 | | 3.16 | 0.16 | 205 | 83 | 27 |
| 202 | VH-Framework-2 | 0.09 | 0 | 205 | 3 | 0 |
| 211 | | 0.03 | 0 | 205 | 1 | 0 |
| 212 | | 0.86 | 0.08 | 205 | 70 | 11 |
| 251 | CDR-H2 | 11.52 | 0.69 | 205 | 163 | 88 |

-continued

| | | antibody-antigen contacts for antigen type 'peptide' | | | | |
|---|---|---|---|---|---|---|
| 1: WolfGuy* Index | 2: region | 3: average amino acid sidechain solvent accessibility change [%] | 4: average number of chemical interactions with antigen | 5: number of samples | 6: number of samples with change of solvent accessible surface | 7: number of samples with chemical interactions with antigen |
| 253 | | 19.04 | 0.96 | 205 | 171 | 105 |
| 254 | | 10.36 | 0.36 | 205 | 104 | 54 |
| 255 | | 8.6 | 0.17 | 164 | 59 | 20 |
| 256 | | 20.46 | 0.46 | 24 | 10 | 6 |
| 287 | | 16.97 | 0.63 | 30 | 22 | 12 |
| 288 | | 7.97 | 0.23 | 205 | 77 | 39 |
| 289 | | 1.57 | 0.05 | 205 | 19 | 6 |
| 290 | | 16.26 | 0.48 | 205 | 128 | 72 |
| 291 | | 0.17 | 0 | 205 | 3 | 1 |
| 292 | | 16.52 | 0.57 | 205 | 147 | 85 |
| 293 | | 0.01 | 0 | 205 | 1 | 0 |
| 294 | | 0.1 | 0 | 205 | 1 | 0 |
| 295 | | 0.51 | 0.01 | 205 | 4 | 2 |
| 296 | | 0.04 | 0 | 205 | 1 | 0 |
| 298 | | 0.19 | 0 | 205 | 6 | 1 |
| 308 | VH-Framework-3 | 0.12 | 0 | 204 | 5 | 1 |
| 311 | | 0.1 | 0 | 202 | 1 | 1 |
| 331 | | 0.17 | 0.01 | 205 | 6 | 2 |
| 332 | | 0.8 | 0.04 | 205 | 26 | 7 |
| 351 | CDR-H3 | 13.89 | 0.74 | 205 | 149 | 89 |
| 352 | | 11.74 | 0.24 | 200 | 79 | 30 |
| 353 | | 22.83 | 0.6 | 178 | 133 | 65 |
| 354 | | 16.42 | 0.43 | 147 | 80 | 42 |
| 355 | | 15.84 | 0.19 | 103 | 49 | 17 |
| 356 | | 5.66 | 0.19 | 53 | 19 | 8 |
| 357 | | 12.4 | 0.54 | 35 | 18 | 9 |
| 358 | | 4.03 | 0.11 | 19 | 5 | 2 |
| 359 | | 6.89 | 0.27 | 11 | 5 | 3 |
| 360 | | 10.98 | 0.5 | 2 | 1 | 1 |
| 388 | | 2.24 | 0 | 7 | 5 | 0 |
| 389 | | 3.22 | 0 | 13 | 1 | 0 |
| 390 | | 16.82 | 0.75 | 28 | 16 | 12 |
| 391 | | 27.86 | 0.39 | 44 | 24 | 12 |
| 392 | | 16.33 | 0.43 | 70 | 40 | 16 |
| 393 | | 20.3 | 0.45 | 84 | 52 | 24 |
| 394 | | 9.27 | 0.3 | 129 | 54 | 27 |
| 395 | | 16.13 | 0.67 | 158 | 105 | 55 |
| 396 | | 3.55 | 0.14 | 174 | 43 | 18 |
| 397 | | 0.73 | 0.03 | 189 | 39 | 6 |
| 398 | | 4.05 | 0.15 | 204 | 39 | 19 |
| 399 | | 0.63 | 0.03 | 205 | 10 | 3 |
| 401 | VH-Framework-4 | 0.08 | 0 | 205 | 4 | 0 |
| 501 | VL-Framework-1 | 0.38 | 0.01 | 160 | 6 | 1 |
| 502 | | 0.28 | 0.01 | 192 | 7 | 1 |
| 555 | CDR-L1 | 1.21 | 0.04 | 26 | 2 | 1 |
| 556 | | 1.17 | 0.05 | 199 | 17 | 6 |
| 561 | | 1.06 | 0.03 | 203 | 9 | 6 |
| 562 | | 0.59 | 0.01 | 199 | 5 | 2 |
| 563 | | 1.2 | 0.01 | 110 | 7 | 1 |
| 571 | | 7.73 | 0.15 | 102 | 34 | 9 |
| 572 | | 9.78 | 0.28 | 43 | 22 | 11 |
| 581 | | 22.13 | 0.85 | 104 | 93 | 62 |
| 582 | | 11.49 | 0.31 | 97 | 36 | 20 |
| 583 | | 10.17 | 0.19 | 78 | 51 | 15 |
| 584 | | 9.45 | 0.11 | 19 | 12 | 2 |
| 594 | | 0.13 | 0 | 97 | 1 | 0 |
| 595 | | 5.3 | 0.23 | 98 | 42 | 18 |
| 596 | | 1.18 | 0.01 | 161 | 10 | 1 |
| 597 | | 17.86 | 0.96 | 205 | 169 | 127 |
| 598 | | 0 | 0 | 205 | 0 | 0 |
| 599 | | 2.67 | 0.23 | 205 | 52 | 37 |
| 602 | VL-Framework-2 | 0.23 | 0.02 | 205 | 18 | 4 |
| 612 | | 1.3 | 0.06 | 205 | 37 | 7 |
| 615 | | 5.24 | 0.24 | 205 | 54 | 34 |
| 651 | CDR-L2 | 7.03 | 0.34 | 205 | 84 | 41 |
| 652 | | 5.76 | 0.2 | 5 | 1 | 1 |
| 653 | | 8.38 | 0 | 5 | 2 | 0 |
| 694 | | 0.62 | 0.04 | 205 | 8 | 8 |
| 695 | | 0.28 | 0 | 205 | 4 | 0 |
| 696 | | 2.25 | 0.05 | 205 | 25 | 9 |

-continued

| | | | | | antibody-antigen contacts for antigen type 'peptide' |
|---|---|---|---|---|---|---|

| 1: WolfGuy* Index | 2: region | 3: average amino acid sidechain solvent accessibility change [%] | 4: average number of chemical interactions with antigen | 5: number of samples | 6: number of samples with change of solvent accessible surface | 7: number of samples with chemical interactions with antigen |
|---|---|---|---|---|---|---|
| 698 | | 0.87 | 0.02 | 205 | 23 | 3 |
| 699 | | 0.99 | 0 | 205 | 9 | 0 |
| 710 | VL-Framework-3 | 0.26 | 0 | 205 | 10 | 1 |
| 711 | | 0.23 | 0 | 205 | 2 | 0 |
| 712 | | 0.03 | 0 | 205 | 1 | 0 |
| 751 | CDR-L3 | 0.8 | 0.06 | 205 | 36 | 12 |
| 752 | | 0.05 | 0 | 205 | 3 | 1 |
| 753 | | 11.07 | 0.55 | 205 | 141 | 63 |
| 754 | | 5.15 | 0.25 | 205 | 77 | 37 |
| 755 | | 10.68 | 0.22 | 190 | 79 | 27 |
| 756 | | 6.57 | 0.18 | 33 | 9 | 4 |
| 757 | | 5.9 | 0.15 | 13 | 3 | 2 |
| 793 | | 2.08 | 0 | 2 | 1 | 0 |
| 794 | | 5.31 | 0 | 19 | 3 | 0 |
| 795 | | 8.91 | 0.26 | 46 | 17 | 5 |
| 796 | | 17.73 | 0.42 | 205 | 148 | 65 |
| 797 | | 2.6 | 0.09 | 205 | 34 | 15 |
| 798 | | 8.42 | 0.57 | 205 | 155 | 81 |
| 799 | | 0.05 | 0 | 205 | 1 | 0 |
| 801 | VL-Framework-4 | 0.03 | 0 | 205 | 3 | 0 |

*Bujotzek, A., et al., Proteins: Structure, Function, and Bioinformatics, 83 (2015) 681-695.

| | | | | | antibody-antigen contacts for antigen type 'protein' |
|---|---|---|---|---|---|---|

| 1: WolfGuy* index | 2: region | 3:average amino acid sidechain solvent accessibility change [%] | 4: average number of chemical interactions with antigen | 5: number of samples | 6: number of samples with change of solvent accessible surface | 7: number of samples with chemical interactions with antigen |
|---|---|---|---|---|---|---|
| 101 | VH-Framework-1 | 1.14 | 0.02 | 405 | 28 | 6 |
| 102 | | 1.17 | 0.01 | 500 | 41 | 5 |
| 103 | | 0.06 | 0 | 518 | 3 | 0 |
| 104 | | 0.02 | 0 | 519 | 1 | 1 |
| 115 | | 0.12 | 0 | 519 | 1 | 0 |
| 116 | | 0.06 | 0 | 519 | 1 | 0 |
| 117 | | 0.17 | 0 | 521 | 3 | 0 |
| 119 | | 0.05 | 0.01 | 521 | 2 | 2 |
| 123 | | 0 | 0 | 521 | 2 | 0 |
| 125 | | 0.19 | 0 | 520 | 5 | 0 |
| 151 | CDR-H1 | 0.92 | 0 | 520 | 16 | 1 |
| 152 | | 1.9 | 0.04 | 518 | 96 | 10 |
| 153 | | 8.44 | 0.11 | 519 | 143 | 45 |
| 154 | | 0.54 | 0.01 | 520 | 13 | 5 |
| 155 | | 8.21 | 0.09 | 520 | 216 | 38 |
| 156 | | 28.18 | 0.37 | 519 | 356 | 133 |
| 157 | | 25.34 | 0.35 | 31 | 21 | 6 |
| 158 | | 1.39 | 0.25 | 4 | 1 | 1 |
| 159 | | 35.95 | 2 | 1 | 1 | 1 |
| 193 | | 36.65 | 1 | 4 | 2 | 2 |
| 194 | | 2.34 | 0.25 | 4 | 1 | 1 |
| 195 | | 29.24 | 0.28 | 46 | 33 | 8 |
| 196 | | 10 | 0.38 | 521 | 274 | 144 |
| 197 | | 16.54 | 0.77 | 521 | 354 | 230 |
| 198 | | 0 | 0 | 521 | 0 | 0 |
| 199 | | 0.94 | 0.06 | 521 | 79 | 24 |
| 209 | VH-Framework-1 | 0.01 | 0 | 521 | 3 | 0 |
| 211 | | 0.05 | 0 | 521 | 8 | 1 |
| 212 | | 0.63 | 0.02 | 521 | 79 | 7 |
| 251 | CDR-H2 | 6.6 | 0.58 | 521 | 282 | 143 |
| 252 | | 0.04 | 0 | 521 | 5 | 1 |
| 253 | | 19.18 | 0.82 | 520 | 424 | 271 |
| 254 | | 11.05 | 0.35 | 521 | 208 | 105 |
| 255 | | 24.42 | 0.54 | 398 | 282 | 132 |
| 256 | | 53.23 | 0.41 | 17 | 15 | 6 |
| 287 | | 37.42 | 0.82 | 22 | 20 | 13 |

-continued

| antibody-antigen contacts for antigen type 'protein' | | | | | | |
| --- | --- | --- | --- | --- | --- | --- |
| 1: WolfGuy* index | 2: region | 3:average amino acid sidechain solvent accessibility change [%] | 4: average number of chemical interactions with antigen | 5: number of samples | 6: number of samples with change of solvent accessible surface | 7: number of samples with chemical interactions with antigen |
| 288 | | 29.29 | 0.6 | 521 | 357 | 196 |
| 289 | | 5.59 | 0.09 | 521 | 108 | 27 |
| 290 | | 31.18 | 0.67 | 521 | 387 | 230 |
| 291 | | 2.34 | 0.02 | 521 | 68 | 10 |
| 292 | | 19.75 | 0.68 | 521 | 351 | 201 |
| 293 | | 0.76 | 0 | 521 | 46 | 1 |
| 294 | | 0.47 | 0 | 521 | 26 | 0 |
| 295 | | 5.24 | 0.12 | 521 | 64 | 25 |
| 296 | | 0.76 | 0.01 | 521 | 18 | 3 |
| 298 | | 3.56 | 0.1 | 521 | 76 | 35 |
| 299 | | 0.42 | 0 | 521 | 6 | 1 |
| 301 | VH-Framework-3 | 0.02 | 0 | 521 | 1 | 0 |
| 303 | | 0.31 | 0 | 521 | 5 | 1 |
| 305 | | 0.27 | 0 | 521 | 7 | 0 |
| 306 | | 0.93 | 0.11 | 521 | 36 | 30 |
| 307 | | 0.19 | 0.01 | 521 | 9 | 3 |
| 308 | | 2.69 | 0.06 | 521 | 74 | 23 |
| 309 | | 2.58 | 0.03 | 521 | 41 | 10 |
| 310 | | 0.22 | 0 | 517 | 6 | 1 |
| 311 | | 0.46 | 0 | 517 | 15 | 0 |
| 316 | | 0.14 | 0 | 521 | 3 | 1 |
| 318 | | 0.22 | 0 | 520 | 3 | 2 |
| 319 | | 0.25 | 0 | 520 | 3 | 0 |
| 331 | | 0 | 0 | 521 | 1 | 1 |
| 332 | | 1.25 | 0.16 | 521 | 104 | 49 |
| 351 | CDR-H3 | 6.84 | 0.37 | 521 | 251 | 136 |
| 352 | | 14.08 | 0.48 | 520 | 266 | 144 |
| 353 | | 30.58 | 0.79 | 478 | 335 | 187 |
| 354 | | 32.67 | 0.81 | 390 | 281 | 165 |
| 355 | | 37.84 | 0.89 | 274 | 201 | 119 |
| 356 | | 27.15 | 0.49 | 130 | 73 | 34 |
| 357 | | 36.05 | 0.94 | 86 | 63 | 43 |
| 358 | | 27.53 | 0.94 | 47 | 33 | 22 |
| 359 | | 26.21 | 0.42 | 24 | 14 | 7 |
| 360 | | 52.84 | 1.38 | 13 | 9 | 8 |
| 361 | | 59.31 | 0.71 | 7 | 6 | 2 |
| 362 | | 30.64 | 1 | 2 | 2 | 1 |
| 363 | | 34.52 | 1 | 1 | 1 | 1 |
| 386 | | 13.44 | 1 | 2 | 2 | 2 |
| 387 | | 48.52 | 2.45 | 11 | 9 | 9 |
| 388 | | 39.49 | 0.47 | 15 | 14 | 4 |
| 389 | | 28.36 | 0.67 | 36 | 23 | 12 |
| 390 | | 42.17 | 0.85 | 61 | 48 | 27 |
| 391 | | 36.31 | 1.06 | 107 | 85 | 52 |
| 392 | | 27.61 | 0.64 | 179 | 124 | 64 |
| 393 | | 25.7 | 0.59 | 223 | 154 | 72 |
| 394 | | 14.43 | 0.5 | 335 | 184 | 86 |
| 395 | | 17.91 | 0.89 | 434 | 291 | 178 |
| 396 | | 2.91 | 0.18 | 467 | 103 | 57 |
| 397 | | 0.5 | 0.02 | 511 | 25 | 6 |
| 398 | | 2.56 | 0.1 | 521 | 99 | 36 |
| 399 | | 1.35 | 0.04 | 521 | 68 | 14 |
| 501 | VL-Framewrok-1 | 1.7 | 0.03 | 421 | 30 | 12 |
| 502 | | 0.52 | 0 | 487 | 41 | 0 |
| 503 | | 0.32 | 0 | 514 | 8 | 0 |
| 504 | | 0 | 0 | 517 | 1 | 0 |
| 505 | | 0.06 | 0 | 518 | 2 | 0 |
| 507 | | 0.31 | 0 | 519 | 3 | 1 |
| 508 | | 0.3 | 0.02 | 434 | 3 | 3 |
| 509 | | 0.29 | 0 | 521 | 2 | 2 |
| 510 | | 0.21 | 0 | 521 | 3 | 1 |
| 511 | | 0.2 | 0 | 521 | 3 | 2 |
| 512 | | 0.19 | 0 | 521 | 3 | 1 |
| 513 | | 0.06 | 0 | 521 | 2 | 0 |
| 514 | | 0.15 | 0 | 521 | 2 | 1 |
| 515 | | 0.12 | 0.01 | 521 | 2 | 1 |
| 516 | | 0.11 | 0 | 521 | 2 | 0 |
| 517 | | 0.24 | 0.01 | 521 | 3 | 2 |
| 518 | | 0.31 | 0.01 | 521 | 7 | 2 |
| 519 | | 0.01 | 0 | 521 | 2 | 0 |

-continued

| antibody-antigen contacts for antigen type 'protein' | | | | | | |
|---|---|---|---|---|---|---|
| 1: WolfGuy* index | 2: region | 3:average amino acid sidechain solvent accessibility change [%] | 4: average number of chemical interactions with antigen | 5: number of samples | 6: number of samples with change of solvent accessible surface | 7: number of samples with chemical interactions with antigen |
| 520 | | 0.16 | 0 | 521 | 4 | 0 |
| 522 | | 0.22 | 0 | 521 | 3 | 0 |
| 551 | CDR-L1 | 0.2 | 0.01 | 521 | 6 | 3 |
| 552 | | 0 | 0 | 521 | 1 | 0 |
| 553 | | 0.17 | 0 | 430 | 3 | 1 |
| 554 | | 0.02 | 0 | 100 | 1 | 0 |
| 555 | | 6.56 | 0.04 | 47 | 8 | 2 |
| 556 | | 4.03 | 0.05 | 511 | 118 | 18 |
| 557 | | 0.11 | 0 | 42 | 1 | 0 |
| 561 | | 5.08 | 0.07 | 501 | 92 | 23 |
| 562 | | 1.15 | 0.01 | 501 | 28 | 5 |
| 563 | | 2.84 | 0.09 | 90 | 10 | 4 |
| 564 | | 37.85 | 0 | 4 | 3 | 0 |
| 571 | | 26.49 | 0.34 | 430 | 294 | 93 |
| 572 | | 11.34 | 0.31 | 96 | 51 | 21 |
| 581 | | 24.92 | 0.68 | 96 | 73 | 37 |
| 582 | | 35.59 | 0.8 | 71 | 49 | 25 |
| 583 | | 40.04 | 0.47 | 43 | 36 | 16 |
| 584 | | 16.68 | 0.29 | 24 | 16 | 7 |
| 594 | | 14.22 | 0.15 | 71 | 25 | 6 |
| 595 | | 19 | 0.59 | 81 | 51 | 31 |
| 596 | | 14.54 | 0.27 | 422 | 188 | 81 |
| 597 | | 21.34 | 0.91 | 521 | 400 | 272 |
| 599 | | 0.62 | 0.02 | 521 | 42 | 9 |
| 602 | VL-Framework-2 | 0.01 | 0 | 521 | 3 | 1 |
| 603 | | 0.03 | 0 | 521 | 1 | 0 |
| 605 | | 0.04 | 0 | 521 | 1 | 0 |
| 608 | | 0.04 | 0 | 521 | 1 | 0 |
| 611 | | 0.07 | 0 | 521 | 1 | 1 |
| 612 | | 0.39 | 0.02 | 521 | 39 | 6 |
| 613 | | 0 | 0 | 521 | 2 | 0 |
| 614 | | 0.02 | 0 | 520 | 1 | 1 |
| 615 | | 7.41 | 0.26 | 519 | 216 | 94 |
| 651 | CDR-L2 | 14.51 | 0.48 | 517 | 296 | 167 |
| 694 | | 1 | 0.04 | 513 | 37 | 21 |
| 695 | | 3.81 | 0.04 | 515 | 86 | 17 |
| 696 | | 12.63 | 0.34 | 517 | 224 | 113 |
| 697 | | 1.21 | 0.02 | 517 | 37 | 5 |
| 698 | | 1.41 | 0.06 | 515 | 72 | 27 |
| 699 | | 8.22 | 0.08 | 515 | 101 | 33 |
| 701 | VL-Framework-3 | 1.21 | 0 | 515 | 13 | 0 |
| 702 | | 0.02 | 0 | 515 | 2 | 1 |
| 703 | | 0.12 | 0 | 516 | 3 | 2 |
| 704 | | 0.78 | 0.01 | 521 | 12 | 3 |
| 705 | | 0.07 | 0.01 | 521 | 2 | 2 |
| 706 | | 0.01 | 0 | 521 | 2 | 0 |
| 707 | | 0.57 | 0 | 521 | 9 | 0 |
| 708 | | 0.02 | 0 | 521 | 1 | 0 |
| 709 | | 0.62 | 0.01 | 521 | 13 | 3 |
| 710 | | 1.18 | 0.06 | 521 | 41 | 21 |
| 711 | | 2.99 | 0.02 | 521 | 81 | 8 |
| 712 | | 1.62 | 0 | 521 | 30 | 0 |
| 715 | | 0.54 | 0 | 521 | 19 | 2 |
| 716 | | 0.16 | 0 | 521 | 5 | 2 |
| 717 | | 0.01 | 0 | 521 | 3 | 0 |
| 718 | | 0.14 | 0 | 521 | 6 | 0 |
| 720 | | 0.09 | 0 | 521 | 3 | 0 |
| 722 | | 0.24 | 0 | 521 | 6 | 1 |
| 723 | | 0.29 | 0 | 520 | 2 | 1 |
| 725 | | 0.22 | 0.01 | 521 | 4 | 2 |
| 726 | | 0.18 | 0 | 521 | 2 | 0 |
| 727 | | 0.25 | 0.01 | 521 | 3 | 1 |
| 728 | | 0.01 | 0 | 521 | 1 | 0 |
| 751 | CDR-L3 | 0.05 | 0.01 | 521 | 10 | 2 |
| 752 | | 0.05 | 0 | 521 | 9 | 1 |
| 753 | | 7.12 | 0.35 | 521 | 272 | 110 |
| 754 | | 13.14 | 0.43 | 495 | 295 | 139 |
| 755 | | 17.95 | 0.25 | 450 | 266 | 78 |
| 756 | | 14.17 | 0.45 | 62 | 21 | 12 |
| 757 | | 19.23 | 0.5 | 2 | 1 | 1 |

-continued

| | | antibody-antigen contacts for antigen type 'protein' | | | | |
|---|---|---|---|---|---|---|
| 1: WolfGuy* index | 2: region | 3: average amino acid sidechain solvent accessibility change [%] | 4: average number of chemical interactions with antigen | 5: number of samples | 6: number of samples with change of solvent accessible surface | 7: number of samples with chemical interactions with antigen |
| 793 | | 4.37 | 0 | 1 | 1 | 0 |
| 794 | | 13.99 | 0.13 | 15 | 6 | 2 |
| 795 | | 8.02 | 0.1 | 99 | 33 | 7 |
| 796 | | 18.2 | 0.43 | 493 | 324 | 138 |
| 797 | | 1.59 | 0.04 | 497 | 55 | 14 |
| 798 | | 5.87 | 0.35 | 521 | 268 | 131 |
| 799 | | 0.95 | 0.01 | 521 | 22 | 3 |
| 810 | VL-Framework-4 | 0.19 | 0 | 496 | 3 | 2 |

*Bujotzek, A., et al. Proteins: Structure, Function, and Bioinformatics 83 (2015) 681-695.

3) Stratification of Selected Back-Mutations (Optional)

If required, to obtain, per single input sequence, multiple variants with an increasing degree of devolution, i.e. reduced binding affinity but maintained binding specificity, mutations can be stacked up in a step-wise process by applying criterion iv), i.e., the average number of antigen interactions in known complex structures, with certain thresholds.

For example, in the initial variant of VL, all positions with an average of more than 0.01 and less than 0.25 antigen interactions are back-mutated to germline, aiming at a very moderate loss of binding affinity. In the next variant, this threshold is raised to 0.5, etc., leading to a growing number of back-mutated positions and an increasing probability of loss of binding affinity.

4) Final Check (Optional)

The sequence variant(s) obtained with the method according to the invention as outlined above can be checked for N-glycosylation sites that might have been introduced while performing the method.

Also duplicate sequences should be removed.

Optionally, an alanine replacement can be performed at a prominent (interaction-prone) position of CDR-H3 to further increase the loss of binding affinity.

The final output of the method according to the current invention is a set of variants of VH and VL sequences of the starting antibody. Combinations of those sequences define antibody variants with different degrees of devolution, i.e., molecules that may have just one matured position replaced by the original germline residue, molecules with several germline replacements in VH and/or VL up to molecules that carry all CDRs of VL as well as CDR-H1 and CDR-H2 in germline configuration.

Specific Example of the Method According to the Invention

The method according to the current invention is exemplified in the following with certain antibodies. This is done simply as exemplification and shall not be construed as limitation of the current invention the true scope thereof is set forth in the appended claims.

To method according to the current invention is demonstrated in the following with three different antibodies with different binding specificities: an anti-CD138 antibody as described in U.S. Pat. No. 9,446,146, an anti-Her2/c-neu antibody as described in U.S. Pat. No. 6,870,034 (see also Hudziak et al. 1989), and an anti-EGFR/Her1 antibody as described in U.S. Pat. No. 6,217,866; all incorporated by reference herein.

The sequences of these antibodies were processed with the method according to the current invention to define VH and VL backmutations for each V sequence. Those were subsequently combined as VL-VH pairs to generate antibody variants. These variants (those with high antigen contact score for each chain have been selected, defined by Kabat positions (Johnson and Wu 2000)) and the resulting VH-VL combinations are listed in the following Table 1.

TABLE 1

Variants in VH and VL of different antibodies. Positions are defined in accordance with the Kabat numbering scheme.

| Identifier | | CDR1 | CDR2 | CDR3 | VH + VL combinations |
|---|---|---|---|---|---|
| CD138 binding site VH | Hw | — | — | — | Hw-Lw |
| | Ha | — | H56 R→S | — | (parent IgG) |
| | Hb | H30 S→T<br>H31 N→G | — | — | Hw-La<br>Hw-Lg |
| | Hg* | H30 S→T<br>H31 N→G | H54 T→S<br>H56 R→S<br>H58 I→N | — | Ha-Lw<br>Ha-La<br>Ha-Lg |
| CD138 binding site VL | Lw | — | — | — | Hb-Lw |
| | La | — | L55 Q→H | — | Hb-La |
| | Lg | L30 N→S | L53 T→S<br>L55 Q→H | — | Hb-Lg<br>Hg-Lw<br>Hg-La<br>Hg-Lg |
| EGFR/Her1 binding site VH | Hw | — | — | — | Hw-Lw |
| | Ha | H31 N→S | — | — | (parent IgG) |
| | Hb | — | H56 N→S | — | Hw-La |
| | Hg* | H31 N→S | H56 N→S | — | Hw-Lb |
| EGFR/Her1 binding site VL | Lw | — | — | — | Hw-Lg |
| | La | L32 N→S | — | — | Ha-Lw |
| | Lb | — | — | L91 →S<br>L93 →S | Hb-Lw<br>Hg-Lw |
| | Lg | L32 N→S | — | L91 →S<br>L93 →S | Hg-Lg |
| Her2/c-neu binding site VH | Hw | — | — | — | Hw-Lw |
| | Ha | H34 I→M | — | — | (parent IgG) |
| | Hb | — | H52 Y→D<br>H53 T→A<br>H56 Y→N<br>H58 R→K | — | Hw-La<br>Hw-Lb<br>Hw-Lg<br>Ha-Lw |
| | Hg* | H34 I→M | H52 Y→D<br>H53 T→A<br>H56 Y→N<br>H58 R→K | — | Hb-Lw<br>Hg-Lw<br>Hg-Lg |

TABLE 1-continued

Variants in VH and VL of different antibodies. Positions are defined in accordance with the Kabat numbering scheme.

| | Iden-tifier | CDR1 | CDR2 | CDR3 | VH + VL combinations |
|---|---|---|---|---|---|
| Her2/ | Lw | — | — | — |
| c-neu | La | L30 N→S | — | |
| binding | Lb | L30 N→S | L53 F→Y | L93 T→S |
| site VL | Lg | L24 R→K | L53 F→Y | L93 T→S |
| | | L30 N→S | L54 L→R | |
| | | | L56 S→T | |

"—" denotes no change.
*'germline' of VH only defined for CDR1 and CDR2.
Sequences that do not deviate from the original input antibody are termed Hw and Lw ('wildtype').
Sequences that have CDRs completely reverted to germline (except for H-CDR3) are termed Lg and Hg* ('germline').

The antibody variants that are listed in Table 1 were produced as humanized IgG1 molecules via CMV-promoter driven transient expression in HEK cells (see Examples and Grote et al. 2012; Thorey et al. 2016). The recombinant antibodies that were secreted into cell culture supernatants were subsequently purified by identical means as their parent antibodies, applying Protein A affinity chromatography followed by SEC. All variants showed a 'benign' behavior with low propensity to aggregate and complete compatibility with standard purification procedures. All antibody derivatives could be purified to homogeneity as demonstrated by SEC and SDS-PAGE. Expression yields of the antibody variants were similar to those of their respective parent antibodies, in the range of 50-300 mg/L culture supernatant. Correct composition and identity of each produced antibody was additionally verified by electrospray ionization mass spectroscopy. None out of the 28 produced variants was associated with unusual/deviant properties or problems during expression, purification and further handling. This indicates that introduction of mutations into Fv with the method according to the current invention does not alter biophysical or expression properties of parent antibodies.

The affinity of the variants was determined using Surface Plasmon Resonance (SPR) with monomeric antigen as analyte (to assess monovalent binding). The on- and off-rates as well as the dissociation constants ($K_D$) of the variable regions of the variants in comparison to their parent antibodies are shown in FIG. 3 for the anti-CD138 antibodies, in FIG. 4 for the anti-Her2/c-neu antibodies and in FIG. 5 for the anti-EGFR/Her1 antibodies.

It can be seen from FIGS. 3 to 5 that with the method according to the current invention variants of all specificities (CD138, Her2/c-neu and EGFR/Her1) yet with different affinities can be generated. The mutations that were introduced to generate these antibodies affected on- as well as off-rates.

The $K_D$ ($k_a/k_d$) of all antibody derivatives always showed either the same/similar, or a reduced affinity compared to parent molecules. Even variants which displayed increased on-rates bound their respective antigens with reduced affinity ($K_D$) as in those faster on-rates were overcompensated by even faster off-rates (e.g. CD138 Hb-Lg antibody, FIG. 3). The influence of different individual mutations and mutation-combinations of on- and off rates (and on resulting $K_D$) is exemplarily shown as SPR-profiles for the parent anti-CD138 antibody and variants thereof in FIG. 6.

Avidity-enhanced specificity requires antibodies that do not bind/retain antigen in a monovalent manner yet show antigen binding in avid settings. In consequence, SPR analyses with monomeric antigen as analyte indicate complete lack of specific binding. The same antibodies, however, display specific antigen binding in SPR assays that cover avidity via bivalent antigen contacts. FIG. 7 shows that the method according to the current invention generates antibodies with those characteristics.

An example for an antibody that requires avidity for effective binding is the CD138-binding antibody Hg-Lw for which antigen binding cannot be detected/evaluated by SPR when immobilizing the antibody and applying monomeric antigen as analyte (FIG. 6, middle sensogram). Addressing the same antibody in an avid binding assay (FIG. 7, middle sensogram), i.e. by inverting the SPR setup (high density immobilization of the target antigen followed by probing with bivalent antibody), specific binding can be detected with 'normal' on-rates and fast off-rates. Other examples of antibody variants show avidity-enhanced binding are the light chain germline back mutated Hw-Lb or Hw-Lg variants of the anti-EGFR/Her1 antibody which bind monovalent with very low affinity ($K_D$ 3.9E-09 or 8.5E-09 M) but retain high affinity binding properties via avidity ($K_D$ 8.0E-10 and 1.0E-10 M respectively). The results for avidity-driven affinity measurements of parent and variant antibodies are shown in FIGS. 8 (anti-CD138 antibodies), 9 (anti-Her2/c-neu antibodies) and 10 (anti-EGFR/Her1 antibodies).

One concern that needs to be addressed when mutating antibody Fv regions towards reduced affinity is that this may affect specificity. In particular general stickiness or polyreactivity may be introduced by such alterations, examples of which being previously reported for antibodies with reduced affinities introduced by alanine replacement (Chuang et al. 2015; Zhu et al. 2011). Therefore, polyreactivity assessments were performed by exposing parent and mutated antibodies to a diverse panel of unrelated antigens including defined proteins such as cardiolipine, heparin, parathyroid hormone, DNA, haemocyanine, streptavidin, BSA, HSP70, insulin, gelatin, albumin, histone, and whole cell lysates derived from E. coli as previously described ((Miller, Pauls, and Fritzler 1991; Mouquet et al. 2010; Khandelwal et al. 2018; Tate and Ward 2004; Finney and Kelsoe 2018; Kelly et al. 2017). The cognate antigens were simultaneously detected in the same ELISA assays to serve as positive controls.

The results of these analyses confirm that affinity reduction via the method according to the current invention does not affect the specificity and does not introduce polyreactivity. The parent CD138 binder, for example (FIG. 11), shows strong reactivity to its cognate antigen but no detectable reactivity to the other probes, with the exception of weak signals upon exposure to E. coli lysates. In a similar manner, variants of said antibody obtained with the method according to the current invention do not elicit increased or additional non-specific signals. Also variants of the anti-Her2/c-neu antibody (FIG. 12) and the anti-EGFR/Her1 antibody (FIG. 13) obtained with the method according to the current invention did not show increased or additional non-specific signals in polyreactivity assessments. Thus, the method according to the current invention generates antibodies with reduced affinity, which however retain their specificity without introduction of polyreactivity.

Comparative Example According to the Art

The currently most frequently applied method to modulate affinity of antibodies is the replacement of CDR residues with alanines (AlaR). Positions for replacement are defined either by random scanning or by structure based choices (Hongo et al. 2000; Vajdos et al. 2002; Kortemme et al. 2004). To compare the method according to the current invention and AlaR procedures, for each of the parental antibodies a variant was generated which harbored alanine instead of germline residues at the positions that deviated from parent antibodies (see Table 2).

TABLE 2

AlaR variants of CD138, EGFR/Her1 and Her2/c-neu. Positions
are defined in accordance with the Rabat numbering scheme.

| | Iden-tifier | CDR1 | CDR2 | CDR3 | VH + VL combinations |
|---|---|---|---|---|---|
| CD138 binding site VH | Hala* | H30 S→A H31 N→A | H54 T→A H56 R→A H58 I→A | — | Hala-Lala |
| CD138 binding site VL | Lala | L30 N→A | L53 T→A L55 Q→A | — | |
| EGFR/ Her1 binding site VH | Hala* | H31 N→A | H56 N→A | — | Hala-Lala |
| EGFR/ Her1 binding site VL | Lala | L32 N→A | — | L91 →A L93 →A | |
| Her2/ c-neu binding site VH | Hala* | H34 I→A | H52 Y→A H53 T→A H56 Y→A H58 R→A | — | Hala-Lala |
| Her2/ c-neu binding site VL | Lala | L24 R→A L30 N→A | L53 F→A L54 L→A L56 S→A | L93 T→A | |

"—" denotes no change.
*Sequences that were previously defined as 'germline' harboring now alanine residues at the same positions.

A comparison of the binding characteristics of those AlaR-derived antibodies with the corresponding parent and invention-derived antibodies is shown in FIGS. 15 to 26.

Interestingly, the method according to the current invention and AlaR resulted in 2 of 3 examples in antibodies with different properties (Table 3).

TABLE 3

Affinities of 'germline' vs AlaR variants. Affinities
were determined in a monovalent (top portion of the
table) and bivalent binding mode (bottom of table).

| | method according to the current invention | | AlaR | |
|---|---|---|---|---|
| specificity | VH-VL combination | $K_D$ [M] | VH-VL combination | $K_D$ [M] |
| monovalent binding mode | | | | |
| CD138 | Hg-Lg | binding not detectable | Hala-Lala | binding not detectable |
| Her2/c-neu | Hg-Lg | 3.9E–07 | Hala-Lala | binding not detectable |
| EGFR/Her1 | Hg-Lg | 1.2E–08 | Hala-Lala | 6.5E–08 |
| bivalent binding mode | | | | |
| CD138 | Hg-Lg | 3.4E–06 | Hala-Lala | 5.1E–07 |
| Her2/c-neu | Hg-Lg | 5.8E–09 | Hala-Lala | binding not detectable |
| EGFR/Her1 | Hg-Lg | 1.0E–11 | Hala-Lala | 4.3E–11 |

32

The 'germline' CD138 binder (generated according to the current invention) and the AlaR variant showed both strongly reduced binding compared to the parental antibody. Her-binding antibody showed divergent properties when comparing the method according to the current invention and the AlaR-derived variant. Polyreactivity assays were also performed (FIG. 14). Her2/c-neu derivatives obtained according to the invention showed significantly reduced affinities compared to parent IgG but still capable to bind in a monovalent as well as bivalent assay setting, while the AlaR generated variant (replacements at the same position), however, abrogated binding to Her2/c-neu (completely in monovalent and reduced to very weak/not detectable in avidity assays). $K_D$ values of parental antibodies see FIGS. 3-5 and 8-10 and tables in 'Example 2'.

Thus, the method according to the current invention is more reliable than AlaR, especially if a set of antibodies that retain specificity (without polyreactivity) and that cover a wide range of reduced affinities needs to be generated. Without being bound by this theory it is assumed that by applying the method according to the current invention the reduction of affinity is not associated with increasing polyreactivity, but also results in a more predictable affinity modulation. This can be seen, e.g., with respect to the mutations of the same positions with alanine instead of germline residues, which modulate affinity in a rather unpredictable manner. Affinities of antibodies generated by AlaR ranged from no effect on affinity (ineffective) to gradually decreased affinity (desired) to complete abrogation (not desired) of binding. In contrast, the method according to the current invention reliably generated for the same parent antibodies sets of variants with increasingly reduced affinities upon increased degree of modification.

Summarizing the above it can be stated that the method according to the current invention, wherein only residues that can unambiguously be defined as mutation-derived are reverted, in consequence can be applied to all animal/human-derived L-chain CDRs and to CDR1 and CDR2 of H-chains. In case of antibodies that carry many mutations in their CDRs vs. their respective germlines the number variants can be regulated by defining preferred choices for germline replacements and—combinations by taking the likelihood of antigen contact for each residue deviating from the germline into account.

While the method according to the current invention in some steps uses structural data, it does not require expert review of the input structure.

Alternatively, the method according to the invention can be performed completely sequence-based wherein the average solvent-accessible surface area and other structural features of a given residue are estimated from a pre-processed structural database, analogously to the statistics on the likelihood of antibody-antigen interactions.

In the method according to the current invention H-chain CDR3 is retained completely in its original composition. In consequence, an antibody with highest degree of modification produced with a method according to the current invention harbors germline sequences in all L-chain CDRs as well as CDR1 and 2 of the H-chains, but retain H-chain CDR3 of the parent antibody.

The following examples, sequences and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 1 Antibody maturation in B-cells.

CITATIONS

Figure 2:
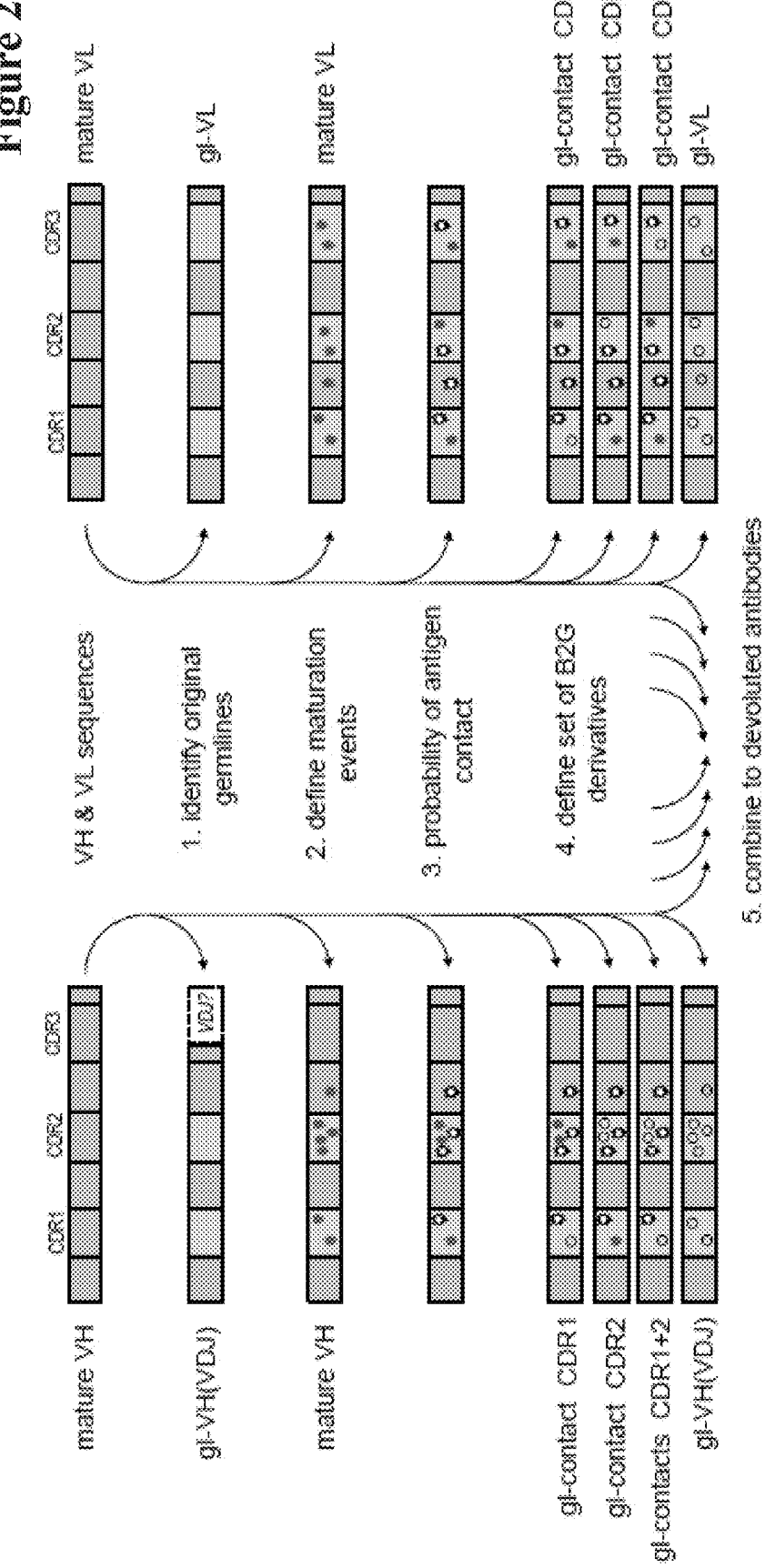
FIG. 2 Antibody de-maturation with a method according to the current invention.
Figure 3:
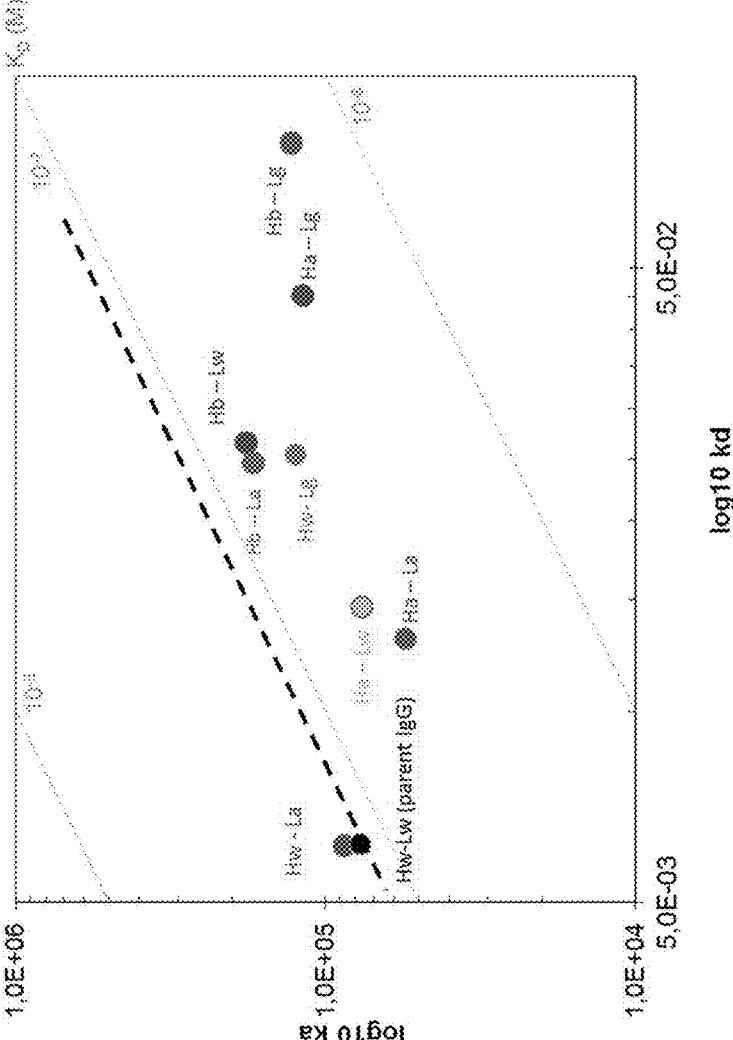
FIG. 3 On-/Off rate plots showing monovalent binding of antibody variants obtained with the method according to the invention to their respective antigens. Surface Plasmon Resonance was applied to measure differences in binding kinetics. This plot shows the data for the anti-CD138 antibody variants of Table 1.
Figure 4:
FIG. 4 On-/Off rate plots showing monovalent binding of antibody variants obtained with the method according to the invention to their respective antigens. Surface Plasmon Resonance was applied to measure differences in binding kinetics. This plot shows the data for the anti-Her2/c-neu antibody variants of Table 1.
Figure 4:
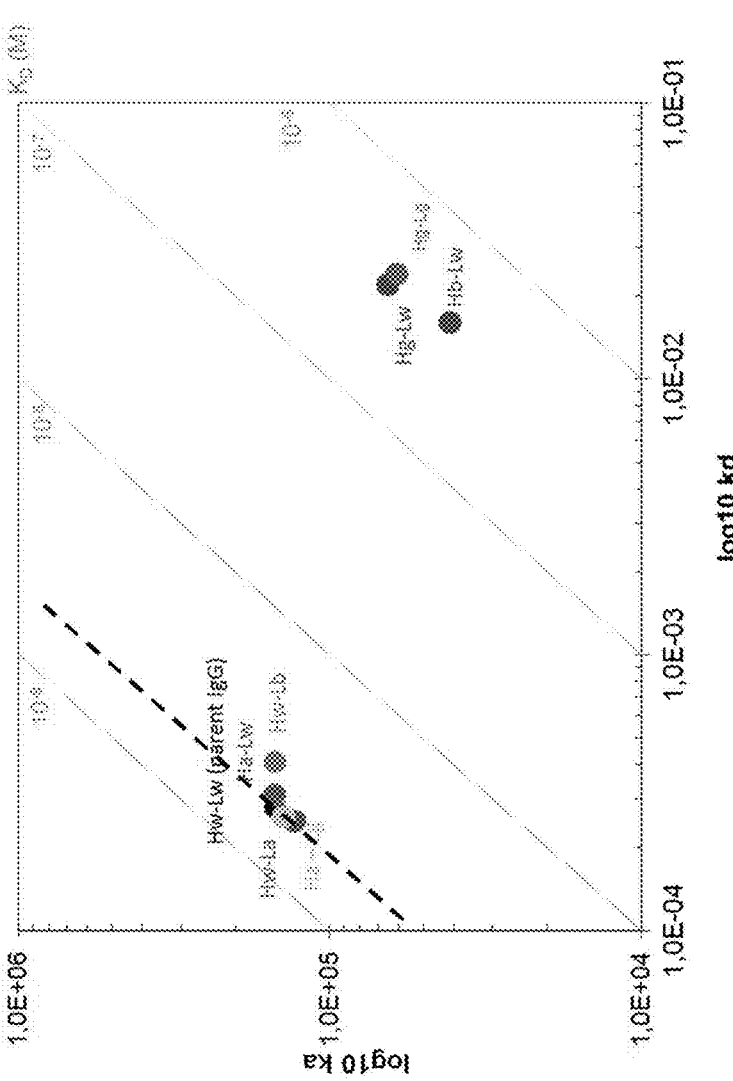
Figure 5:
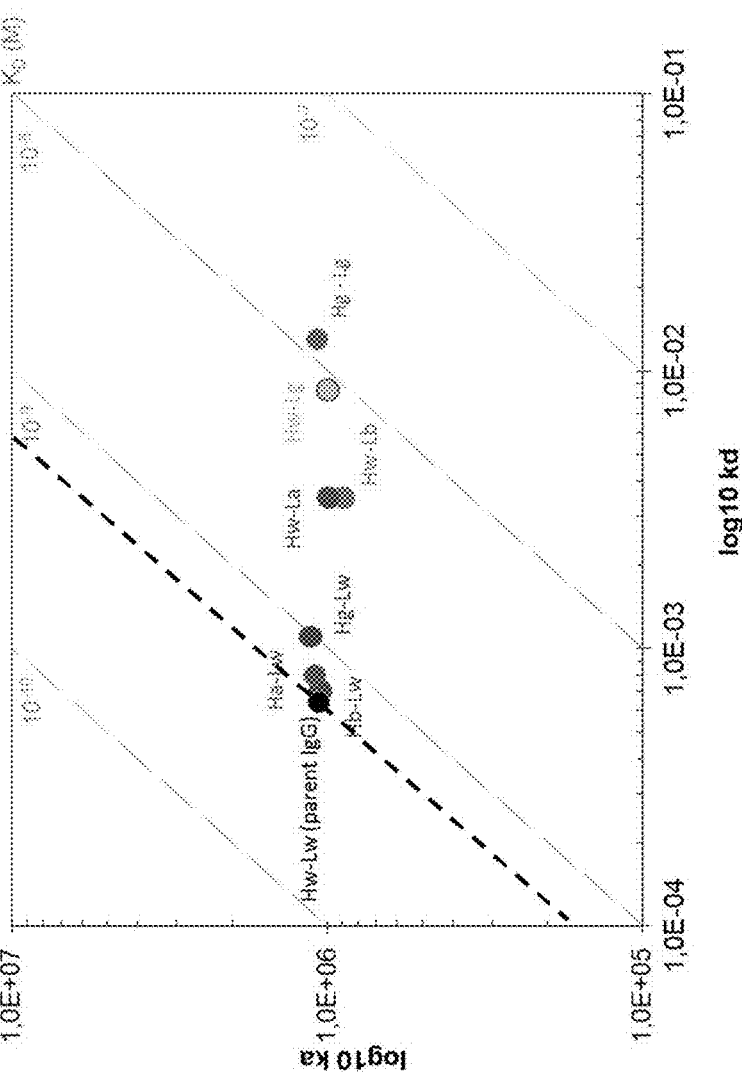
FIG. 5 On-/Off rate plots showing monovalent binding of antibody variants obtained with the method according to the invention to their respective antigens. Surface Plasmon Resonance was applied to measure differences in binding kinetics. This plot shows the data for the anti-Her 1 antibody variants of Table 1.
Figure 6:
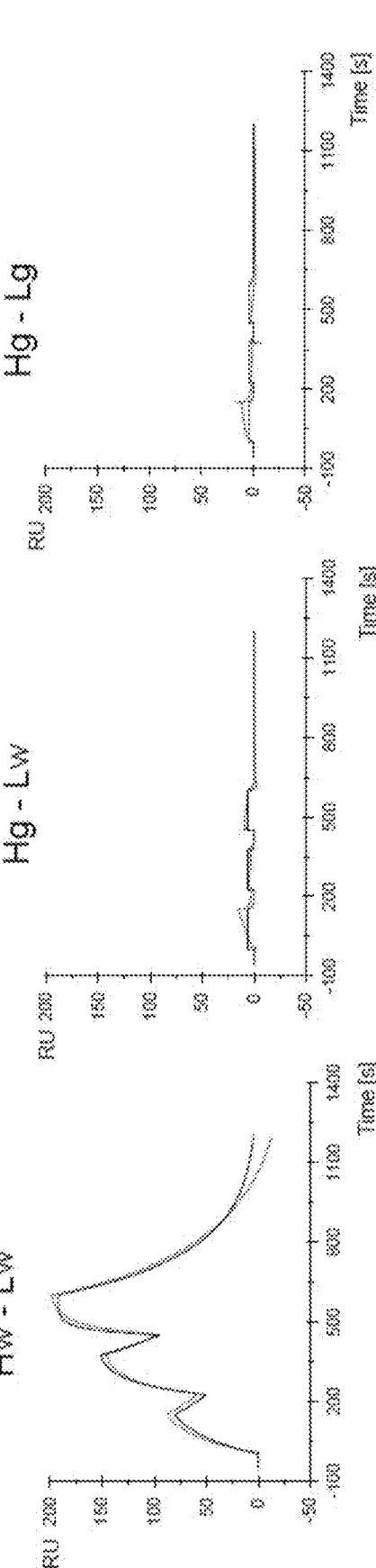
FIG. 6 Binding of parent anti-CD138 antibody and to variants obtained with the method according to the current invention to CD138. Surface Plasmon Resonance with monomeric CD138 protein as analyte assesses monovalent binding.
Figure 7:
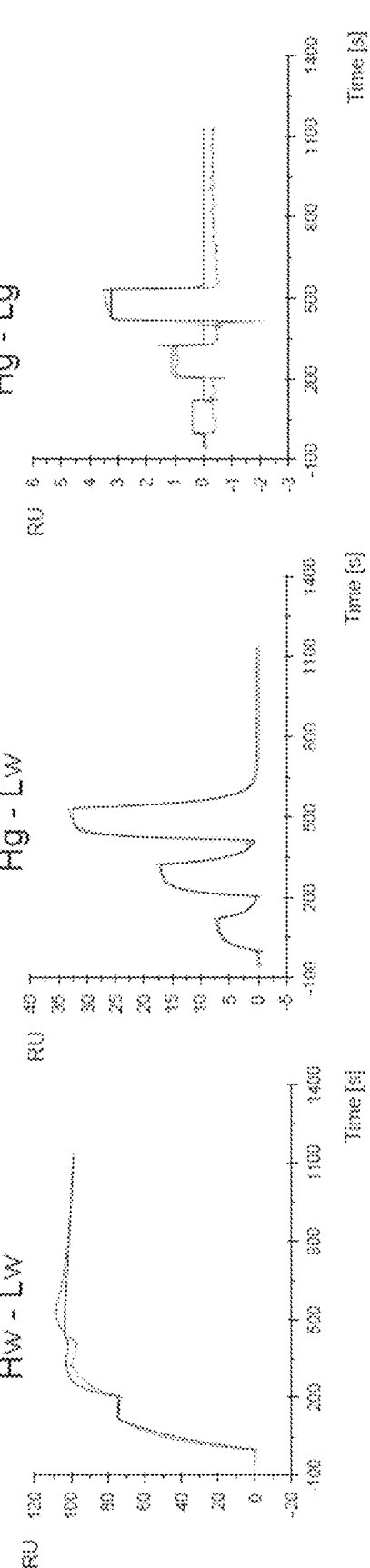
FIG. 7 Binding of parent anti-CD138 antibody and to variants obtained with the method according to the current invention to CD138. Surface Plasmon Resonance with monomeric CD138 protein as analyte assesses bivalent binding.
Figure 8:
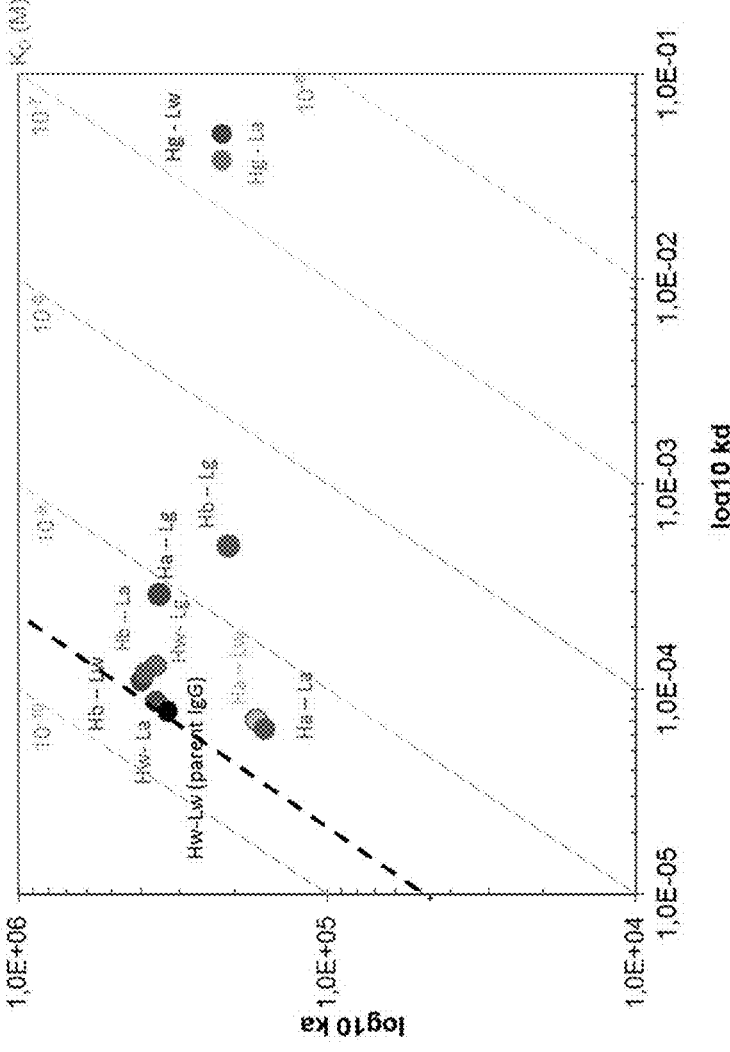
FIG. 8 On-/Off rate plots showing bivalent binding of antibody variants obtained with the method according to the invention to their respective antigens. Surface Plasmon Resonance was applied to measure differences in binding kinetics. This plot shows the data for the anti-CD138 antibody variants of Table 1.
Figure 9:
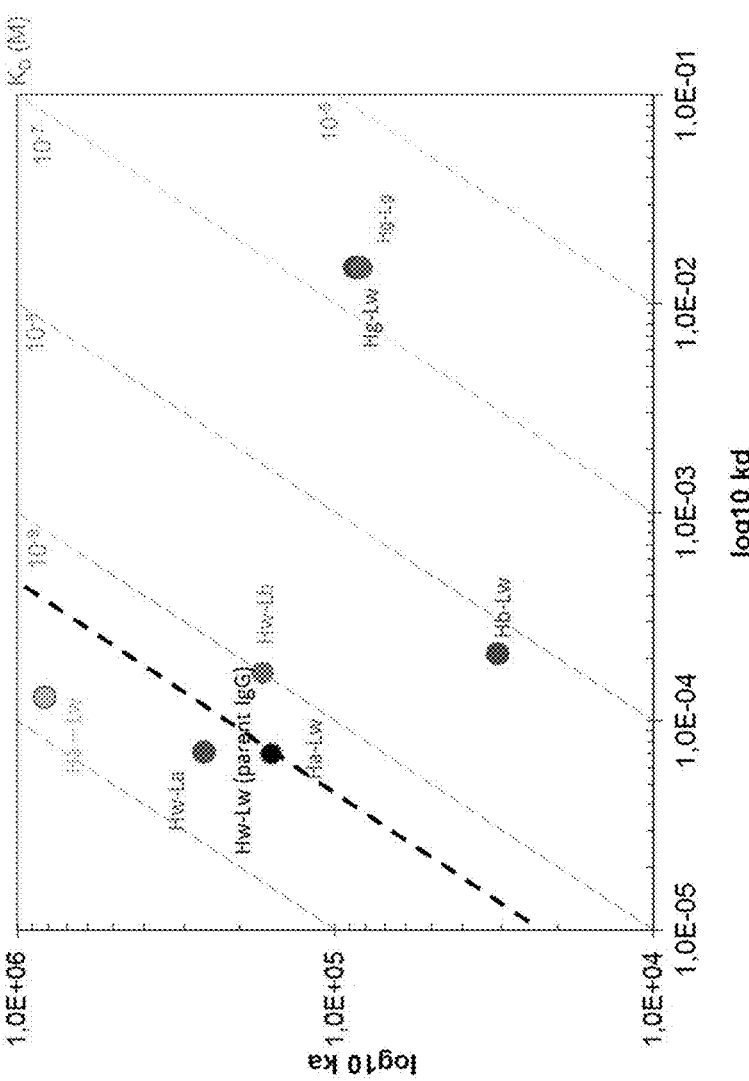
FIG. 9 On-/Off rate plots showing bivalent binding of antibody variants obtained with the method according to the invention to their respective antigens. Surface Plasmon Resonance was applied to measure differences in binding kinetics. This plot shows the data for the anti-Her2/c-neu antibody variants of Table 1.
Figure 10:
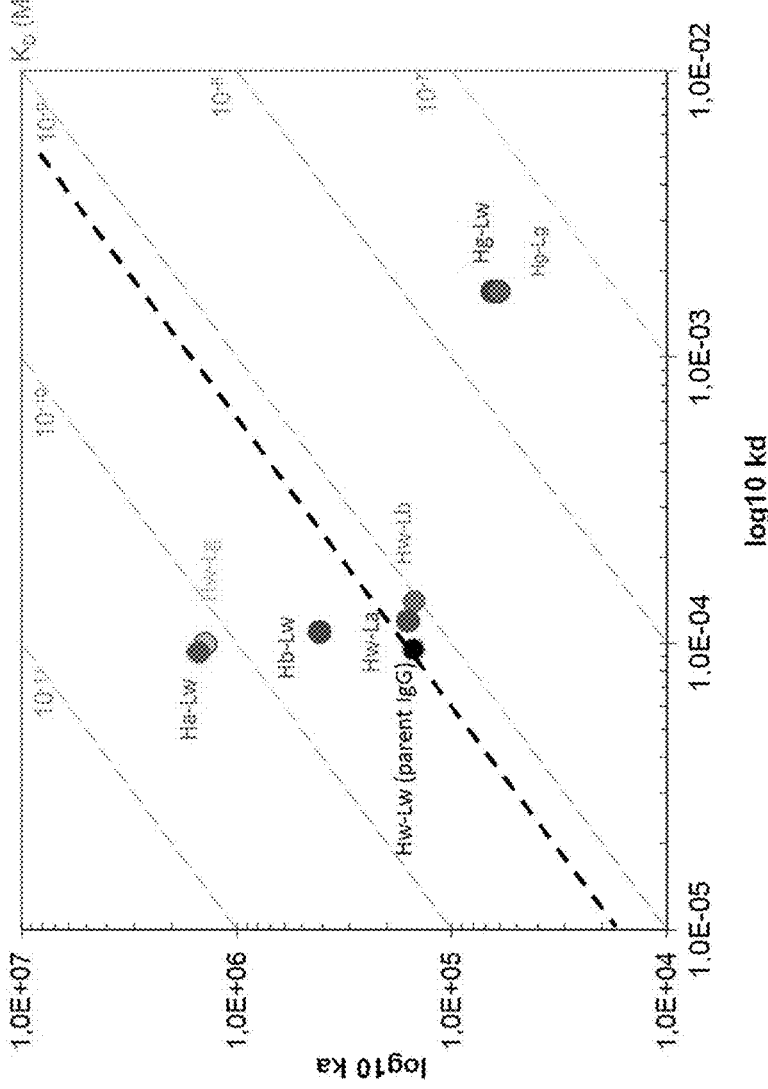
FIG. 10 On-/Off rate plots showing bivalent binding of antibody variants obtained with the method according to the invention to their respective antigens. Surface Plasmon Resonance was applied to measure differences in binding kinetics. This plot shows the data for the anti-Her 1 antibody variants of Table 1.
Figure 11:
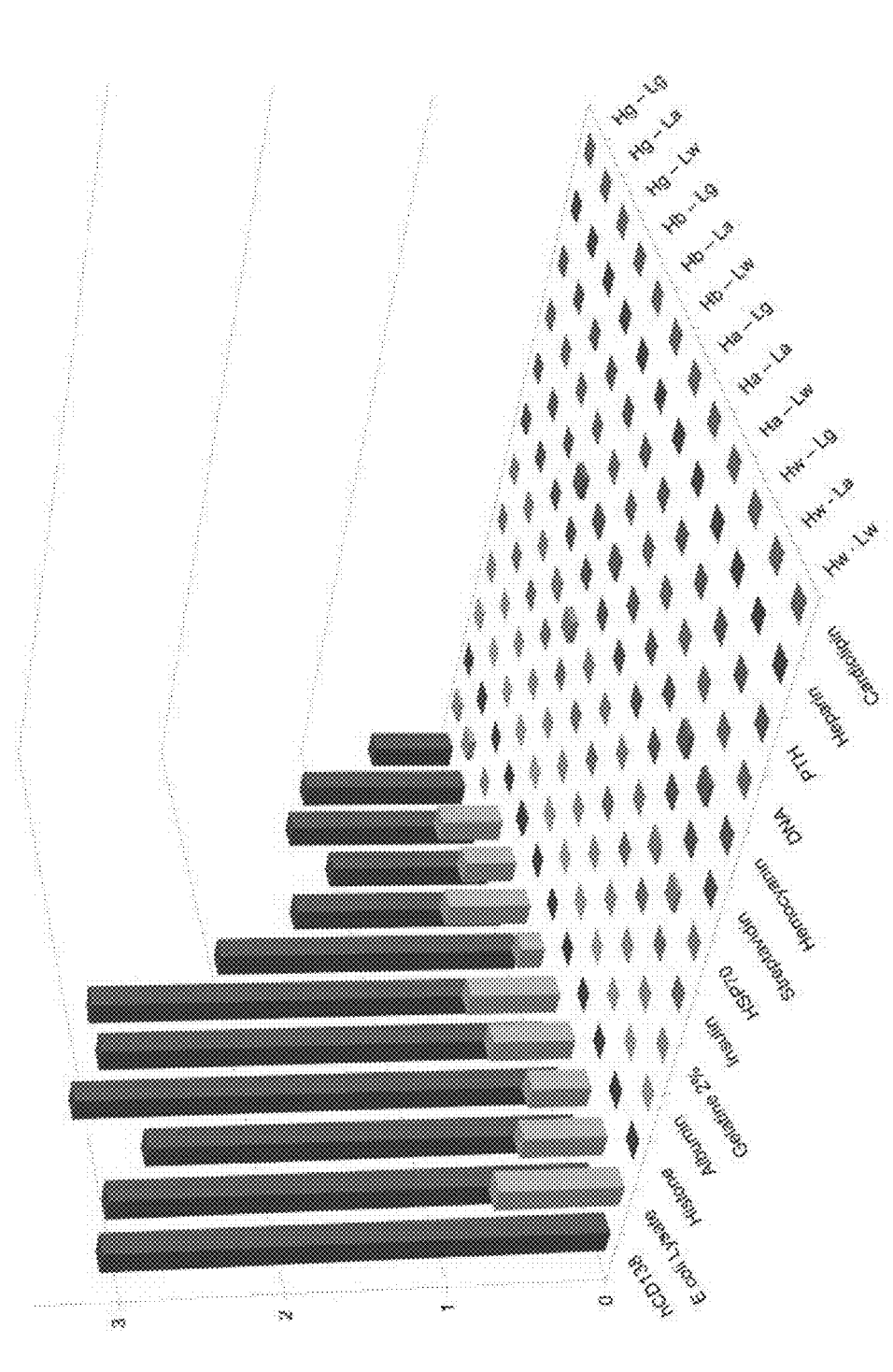
FIG. 11 ELISA-based polyreactivity assessment of anti-CD138 antibody variants obtained with the method according to the current invention. X-axis: absorption at 370 nm.
Figure 12:
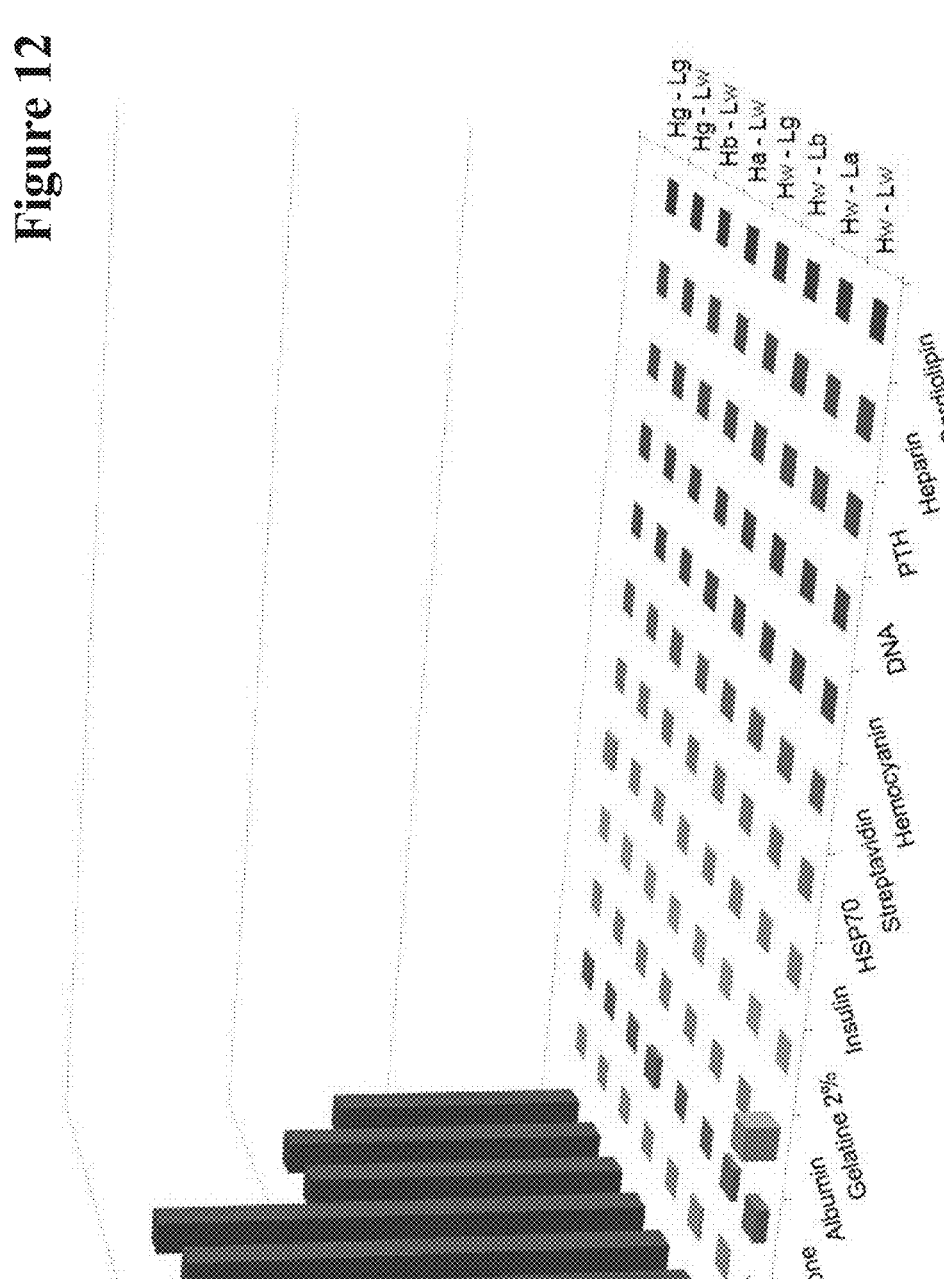
FIG. 12 ELISA-based polyreactivity assessment of anti-Her2/c-neu antibody variants obtained with the method according to the current invention. X-axis: absorption at 370 nm.
Figure 13:
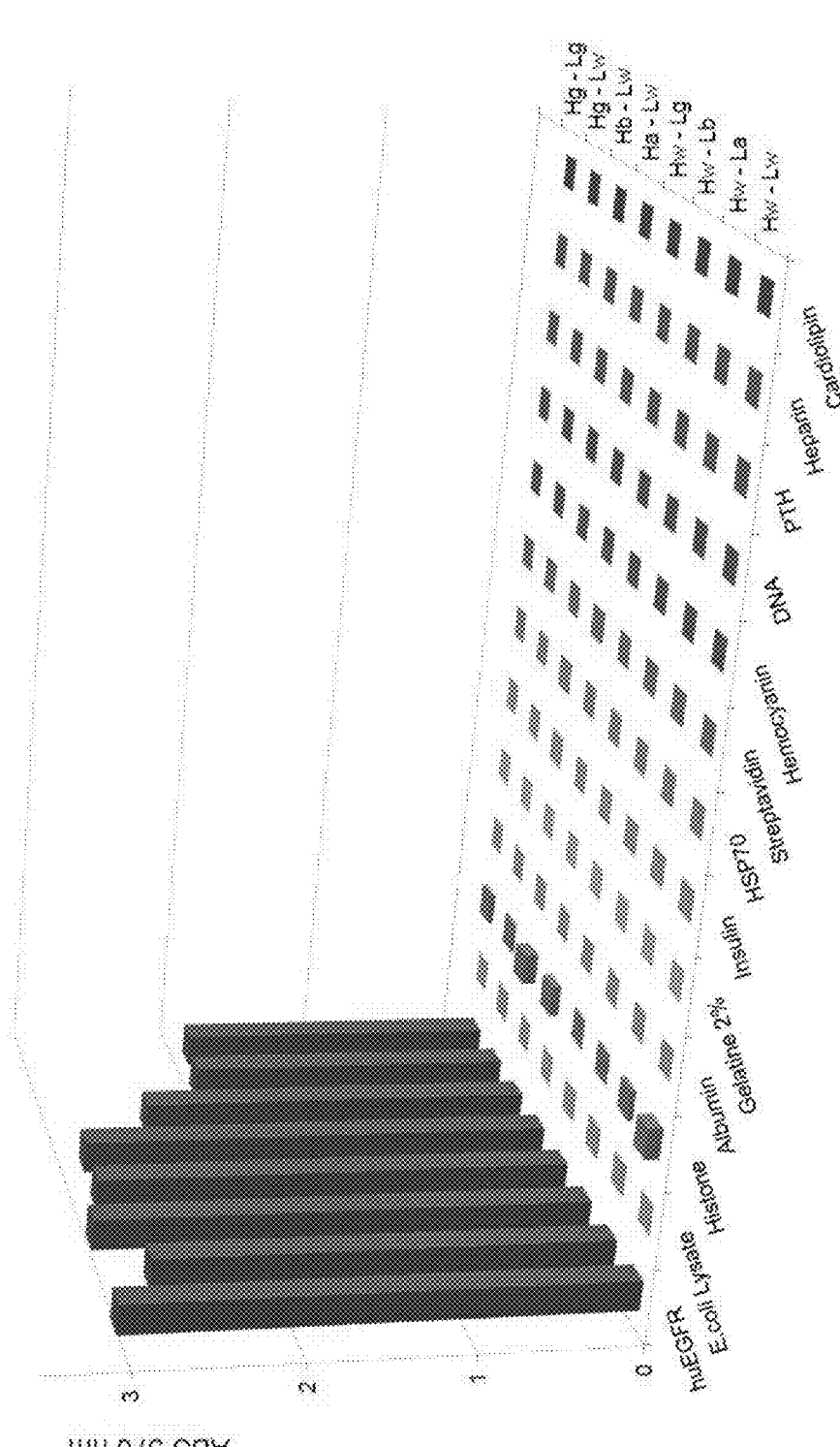
FIG. 13 ELISA-based polyreactivity assessment of anti-EGFR/Her1 antibody variants obtained with the method according to the current invention. X-axis: absorption at 370 nm.
Figure 14:
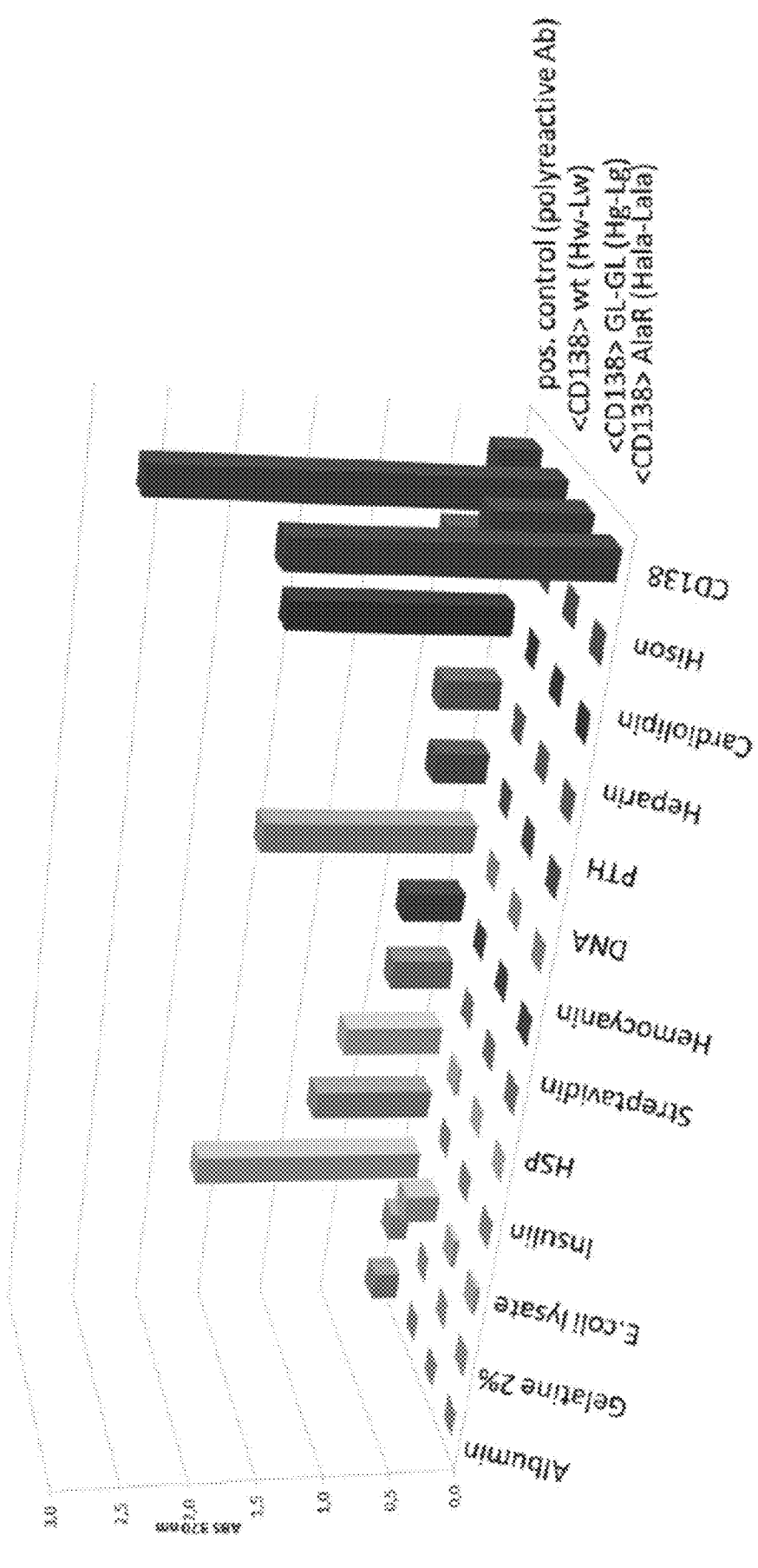
FIG. 14 ELISA-based polyreactivity assessment of anti-CD138 antibody variants obtained with the method according to the current invention and with alanine scanning. X-axis: absorption at 370 nm.
Figure 15:
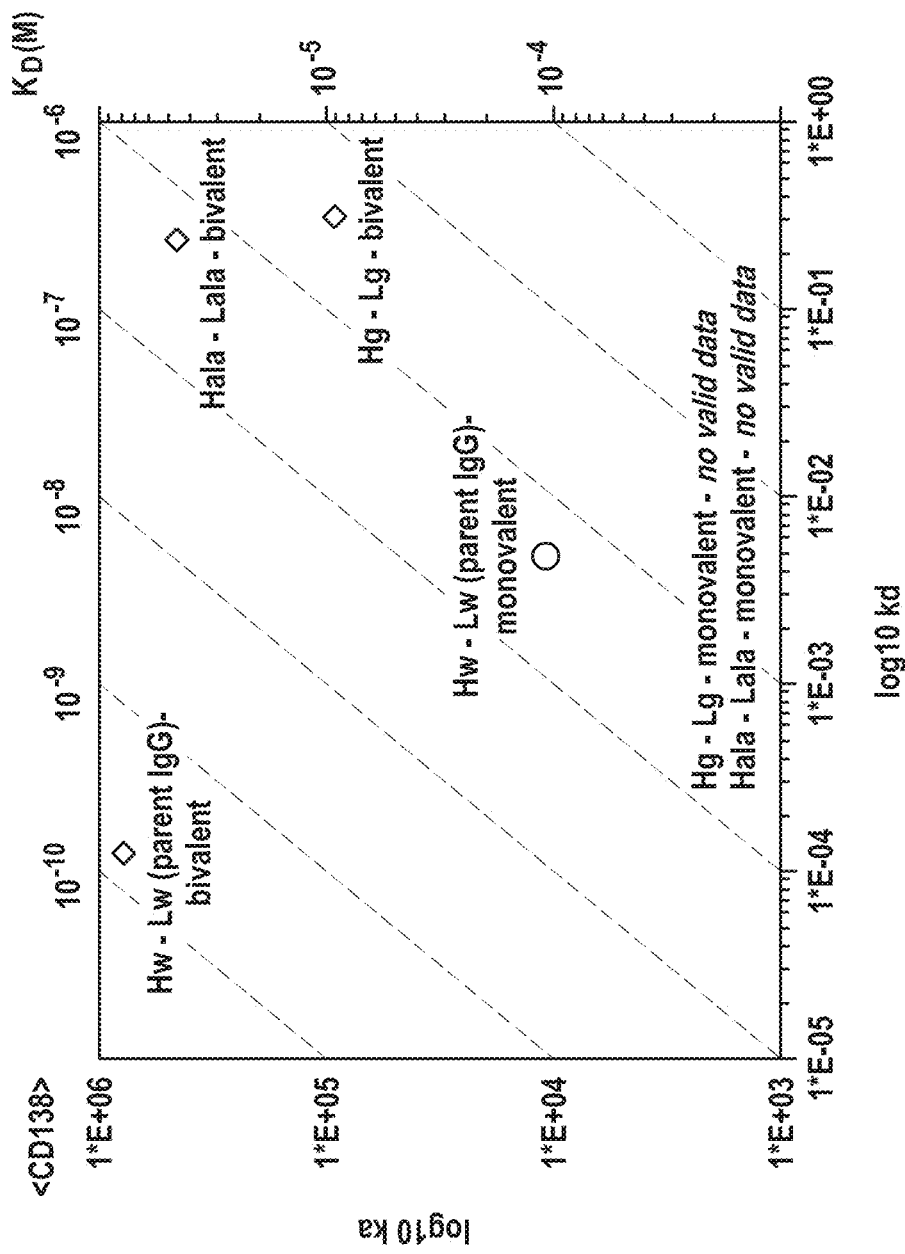
FIG. 15 A comparison of the binding characteristics of AlaR-derived anti-CD138 antibody with the corresponding parent and invention-derived antibodies. Shown is an on-/off-rate plot.
Figure 16:
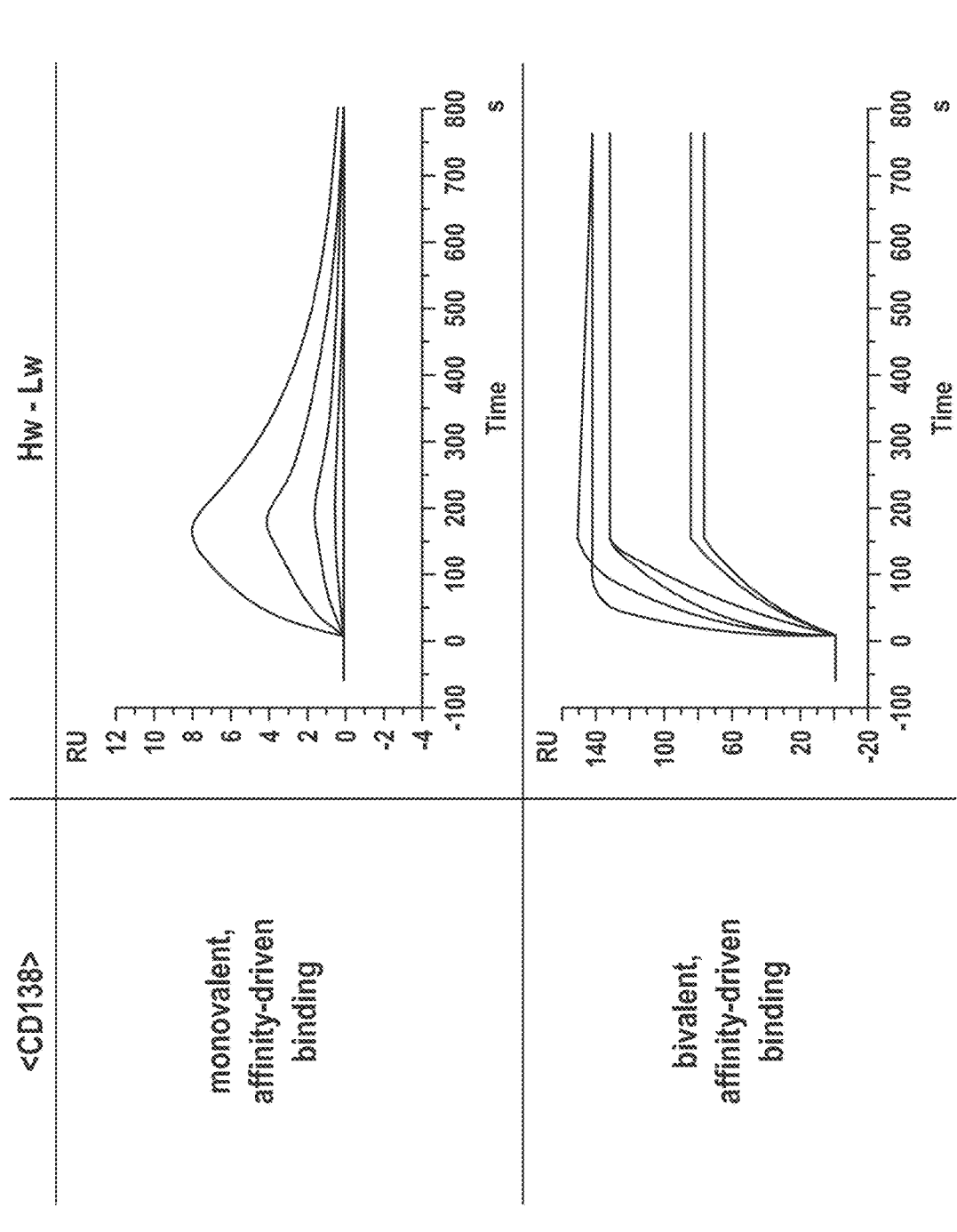
FIG. 16 A comparison of the binding characteristics of AlaR-derived anti-CD138 antibody with the corresponding parent and invention-derived antibodies. Shown are SPR profiles based on affinity-mediated and avidity-mediated binding kinetics for the Hw-Lw combination.
Figure 17:
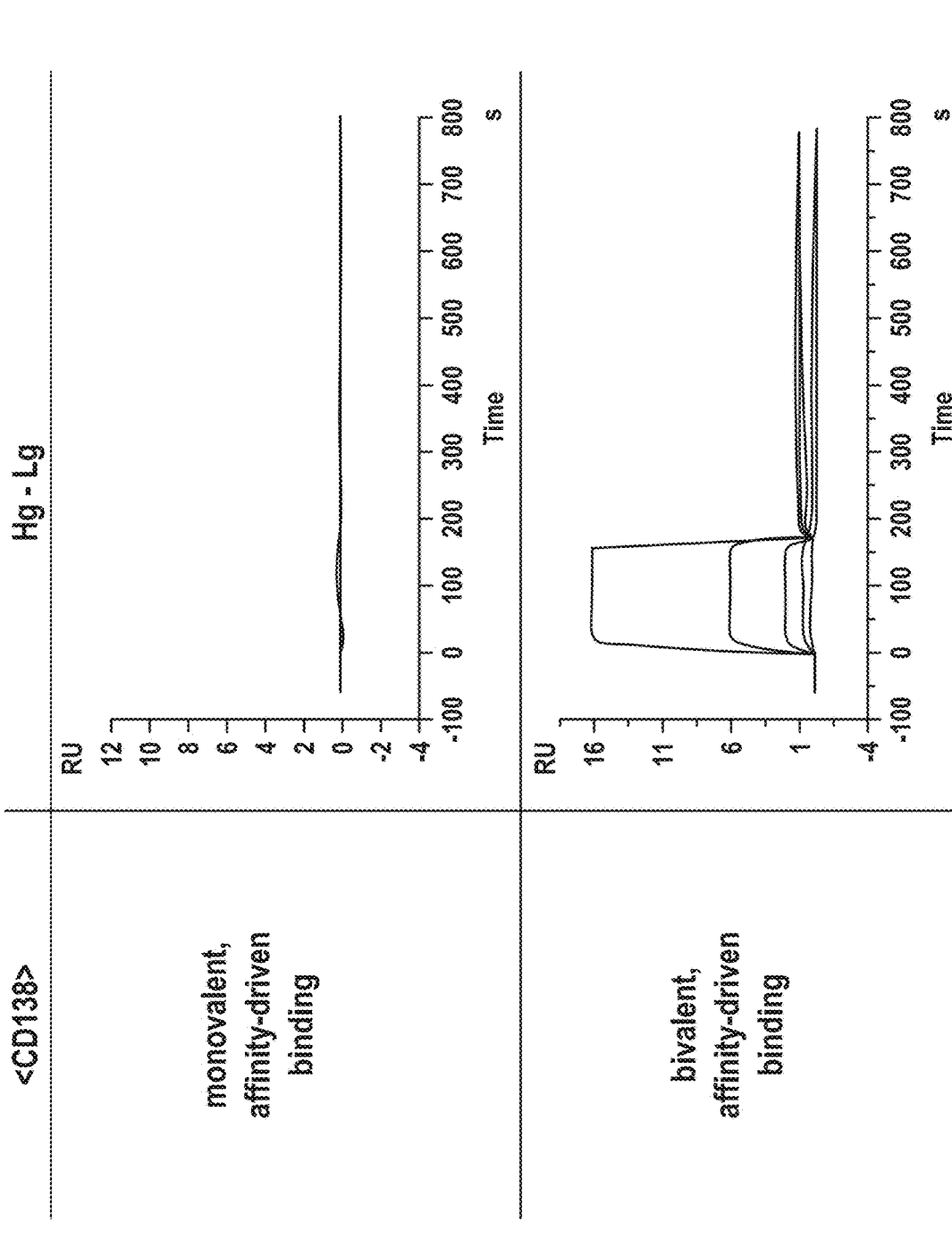
FIG. 17 A comparison of the binding characteristics of AlaR-derived anti-CD138 antibody with the corresponding parent and invention-derived antibodies. Shown are SPR profiles based on affinity-mediated and avidity-mediated binding kinetics for the Hg-Lg combination.
Figure 18:
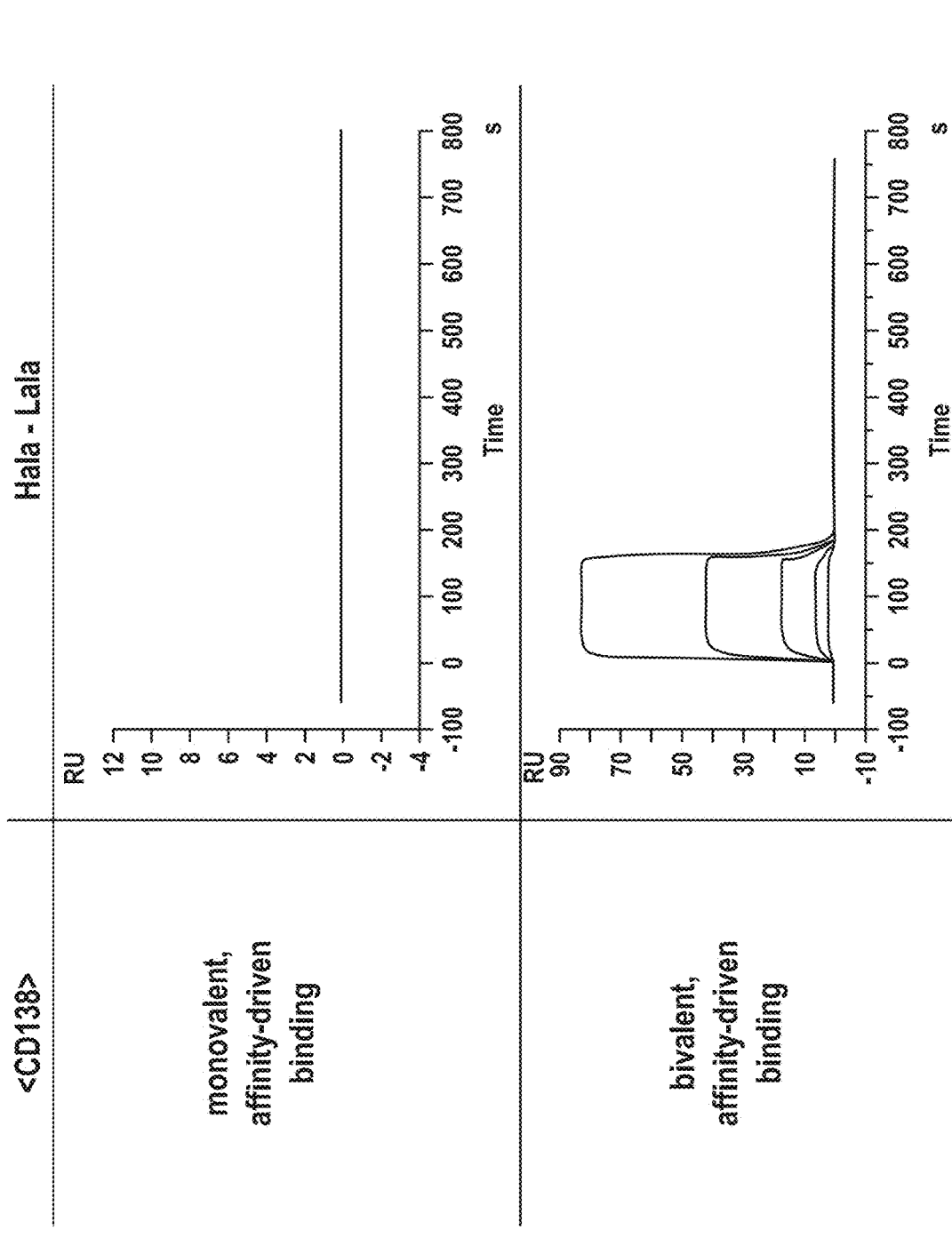
FIG. 18 A comparison of the binding characteristics of AlaR-derived anti-CD138 antibody with the corresponding parent and invention-derived antibodies. Shown are SPR profiles based on affinity-mediated and avidity-mediated binding kinetics for the Hala-Lala combination.
Figure 19:
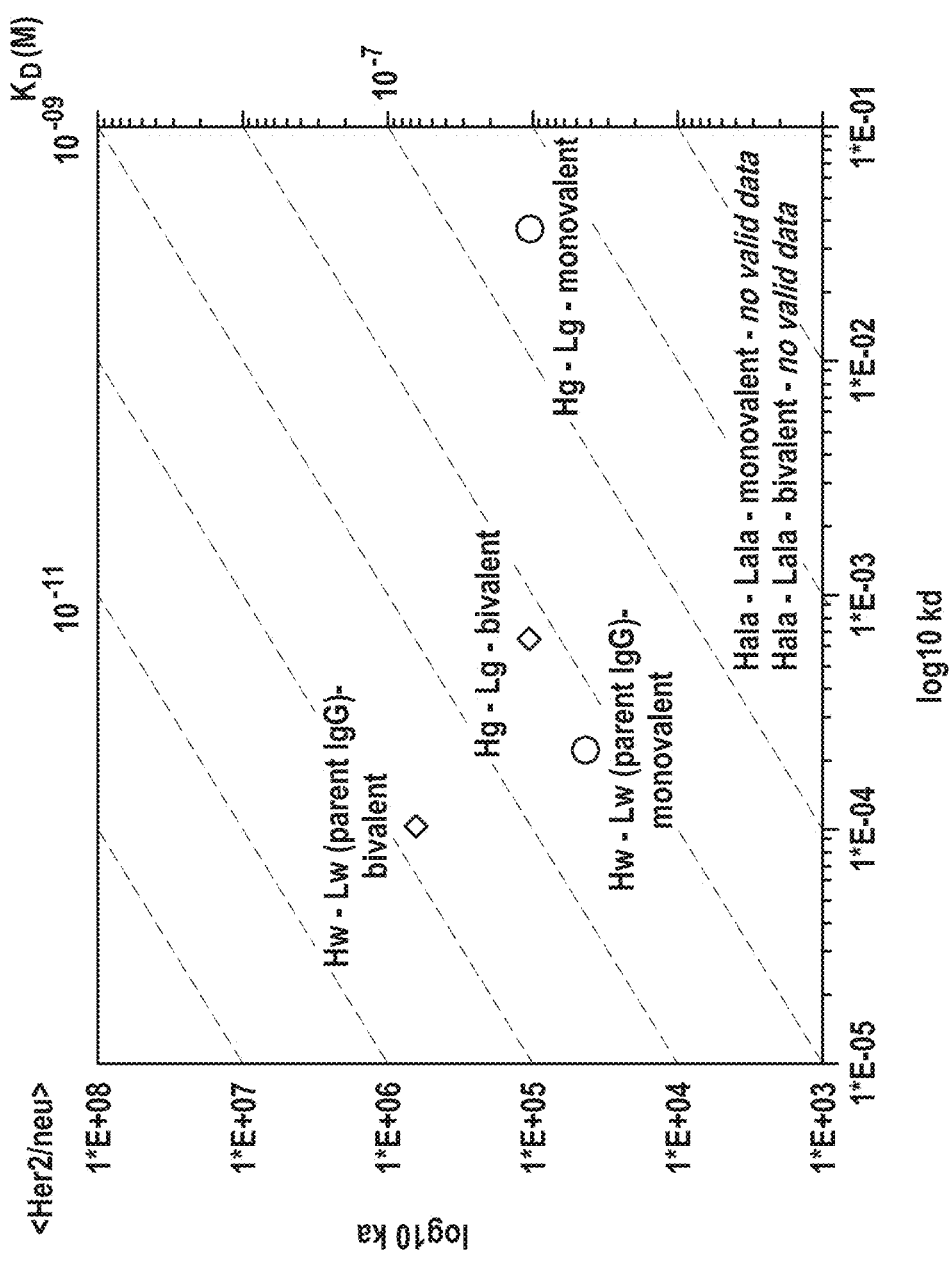
FIG. 19 A comparison of the binding characteristics of AlaR-derived anti-Her 2 antibody with the corresponding parent and invention-derived antibodies. Shown is an on-/off-rate plot.
Figure 20:
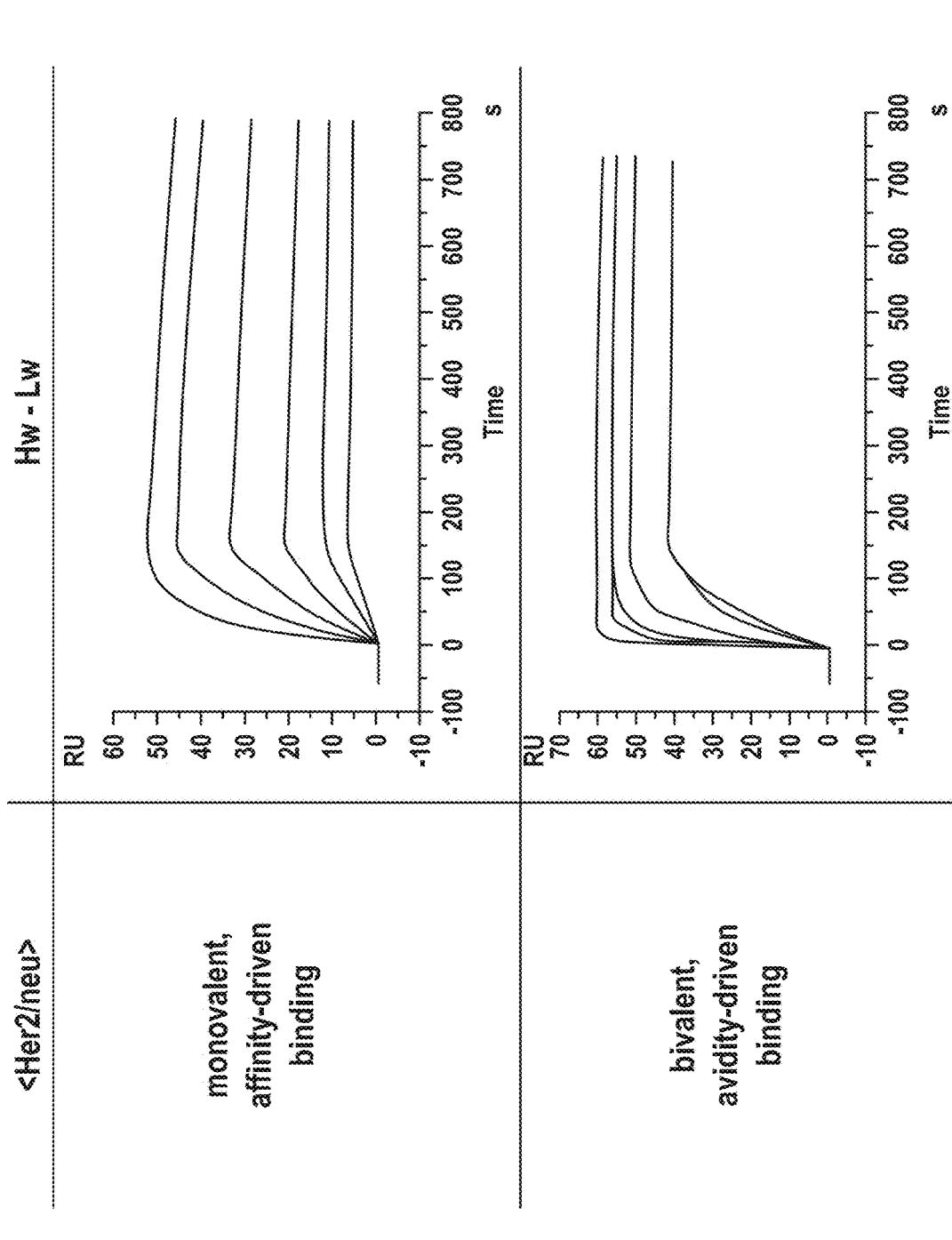
FIG. 20 A comparison of the binding characteristics of AlaR-derived anti-Her 2 antibody with the corresponding parent and invention-derived antibodies. Shown are SPR profiles based on affinity-mediated and avidity-mediated binding kinetics for the Hw-Lw combination.
Figure 21:
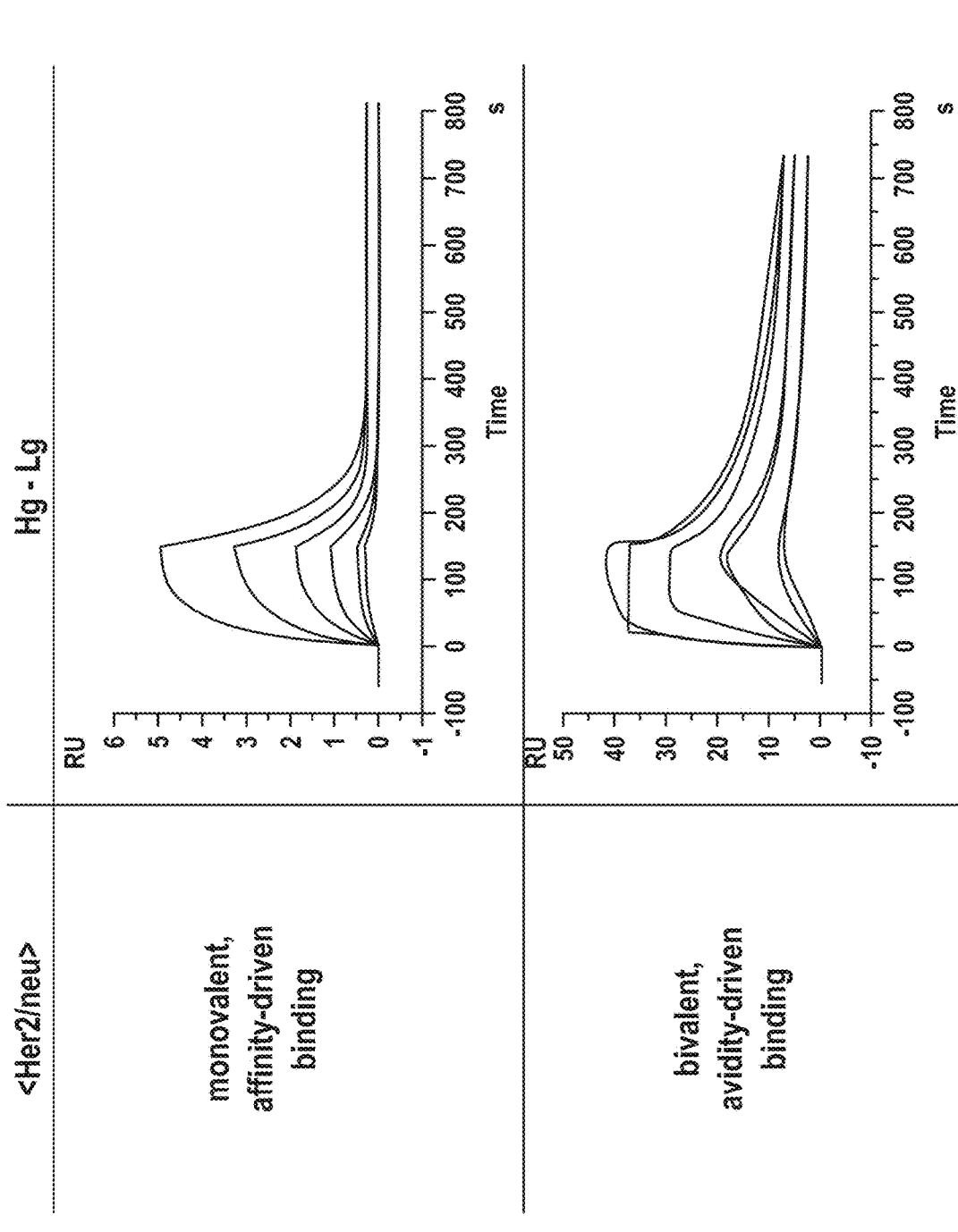
FIG. 21 A comparison of the binding characteristics of AlaR-derived anti-Her 2 antibody with the corresponding parent and invention-derived antibodies. Shown are SPR profiles based on affinity-mediated and avidity-mediated binding kinetics for the Hg-Lg combination.
Figure 22:
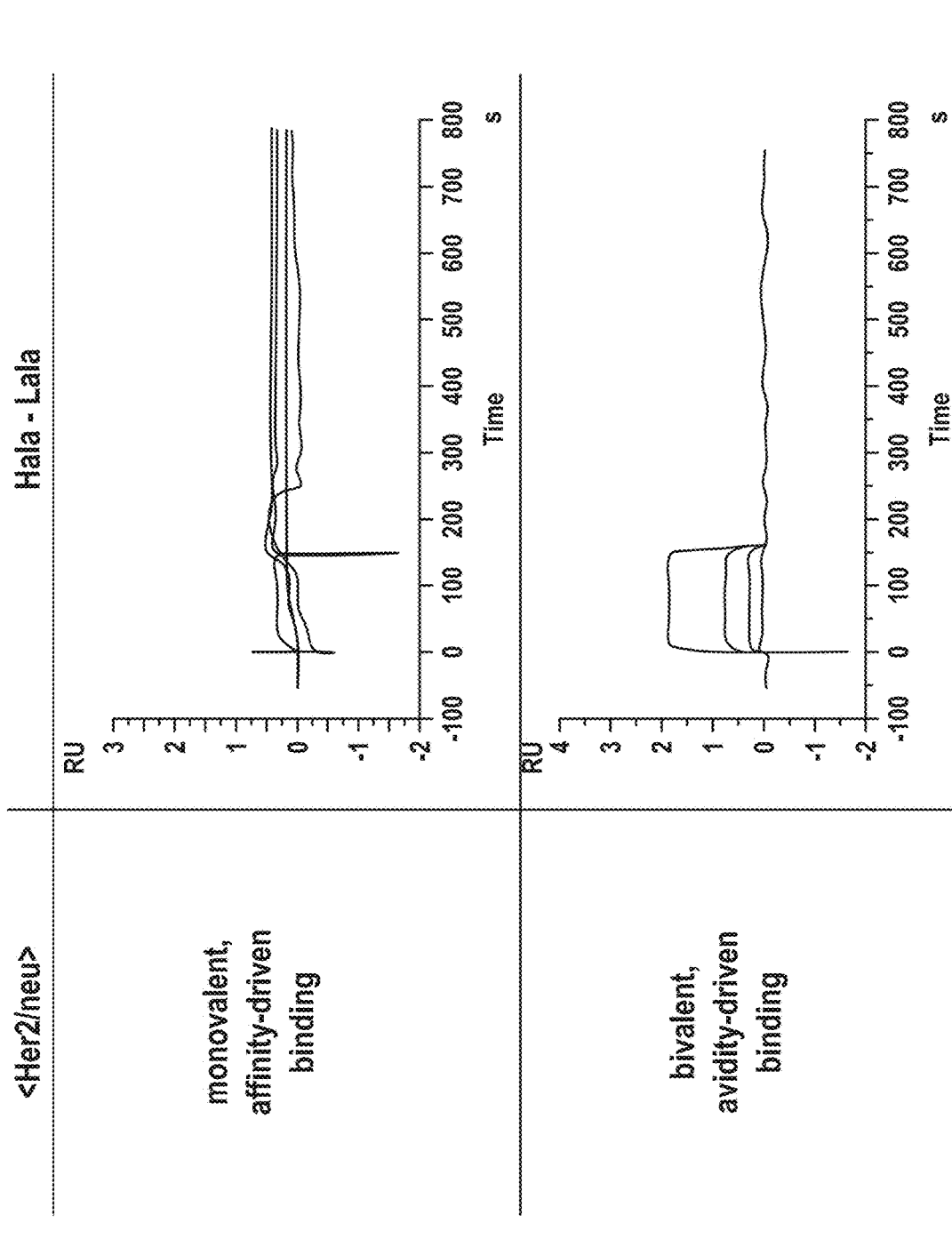
FIG. 22 A comparison of the binding characteristics of AlaR-derived anti-Her 2 antibody with the corresponding parent and invention-derived antibodies. Shown are SPR profiles based on affinity-mediated and avidity-mediated binding kinetics for the Hala-Lala combination.
Figure 23:
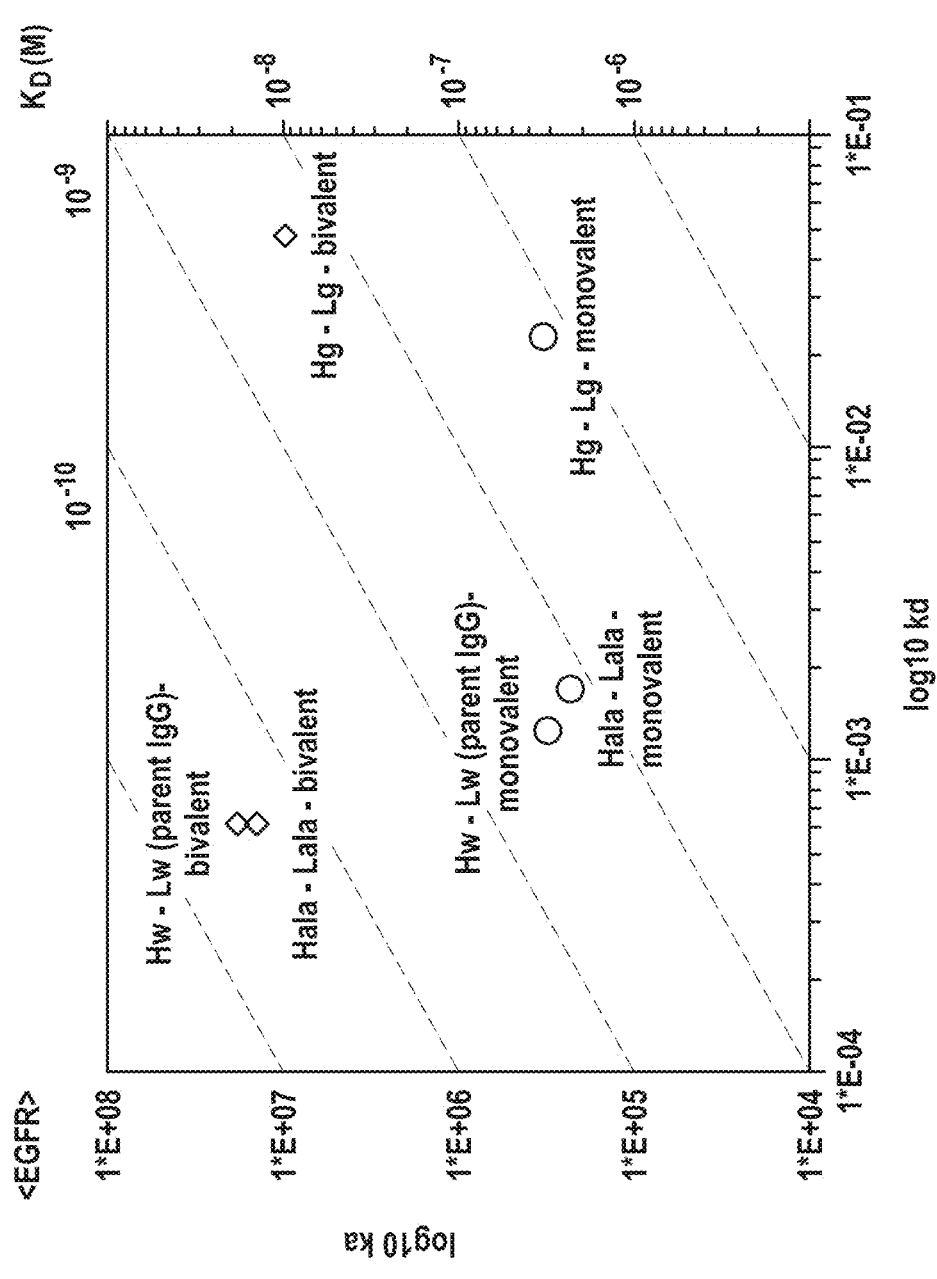
FIG. 23 A comparison of the binding characteristics of AlaR-derived anti-EGFR/Her1 antibody with the corresponding parent and invention-derived antibodies. Shown is an on-/off-rate plot.
Figure 24:
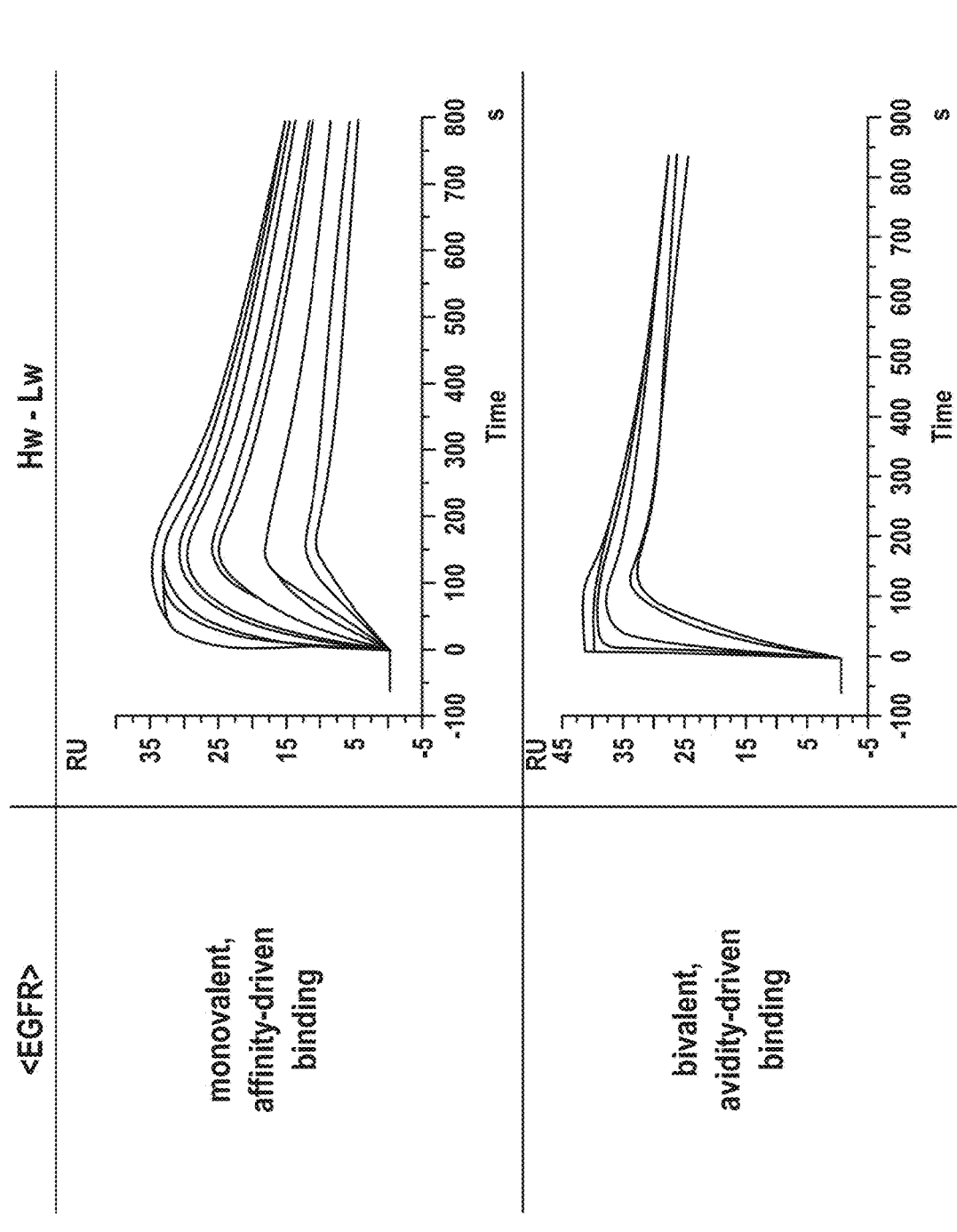
FIG. 24 A comparison of the binding characteristics of AlaR-derived anti-EGFR/Her1 antibody with the corresponding parent and invention-derived antibodies. Shown are SPR profiles based on affinity-mediated and avidity-mediated binding kinetics for the Hw-Lw combination.
Figure 25:
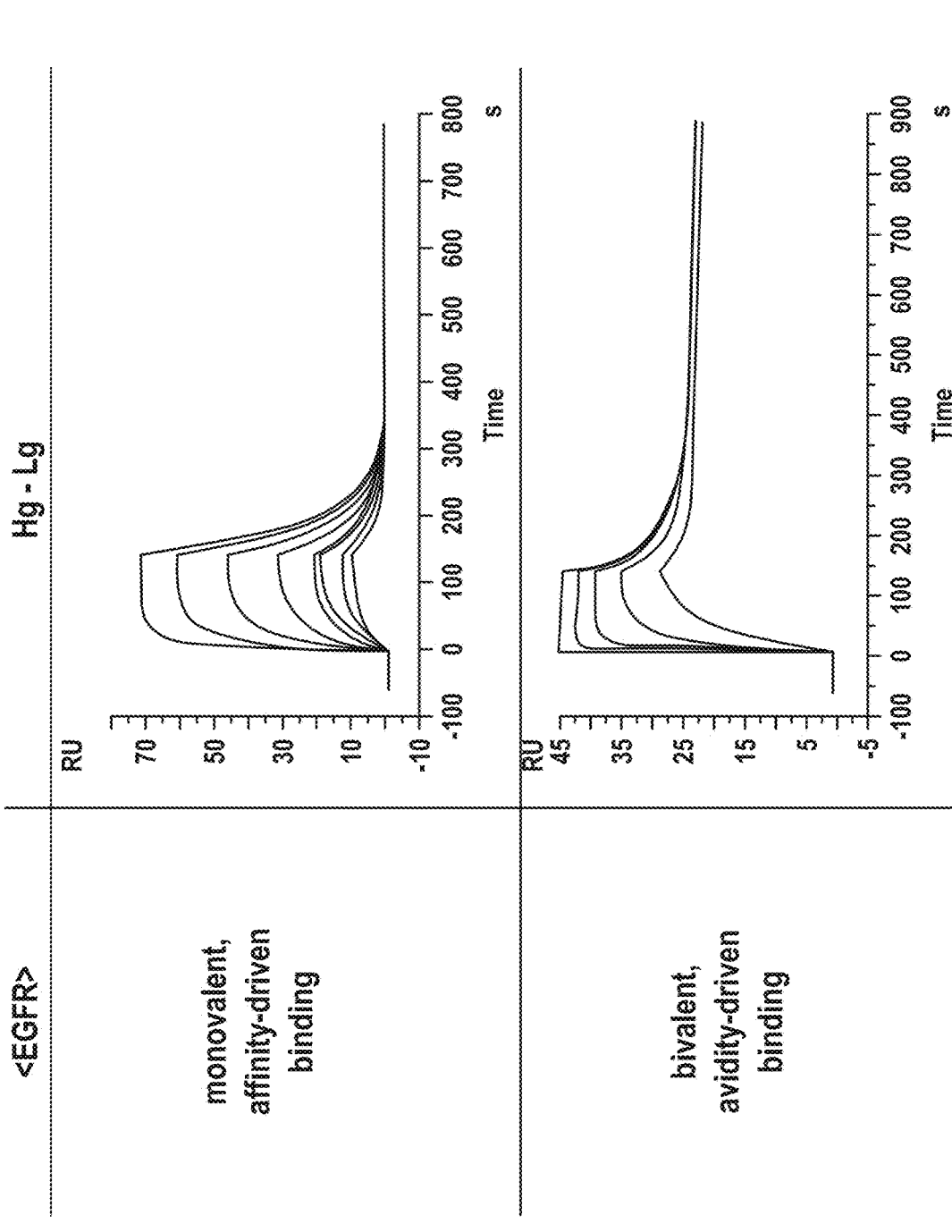
FIG. 25 A comparison of the binding characteristics of AlaR-derived anti-EGFR/Her1 antibody with the corresponding parent and invention-derived antibodies. Shown are SPR profiles based on affinity-mediated and avidity-mediated binding kinetics for the Hg-Lg combination.
Figure 26:
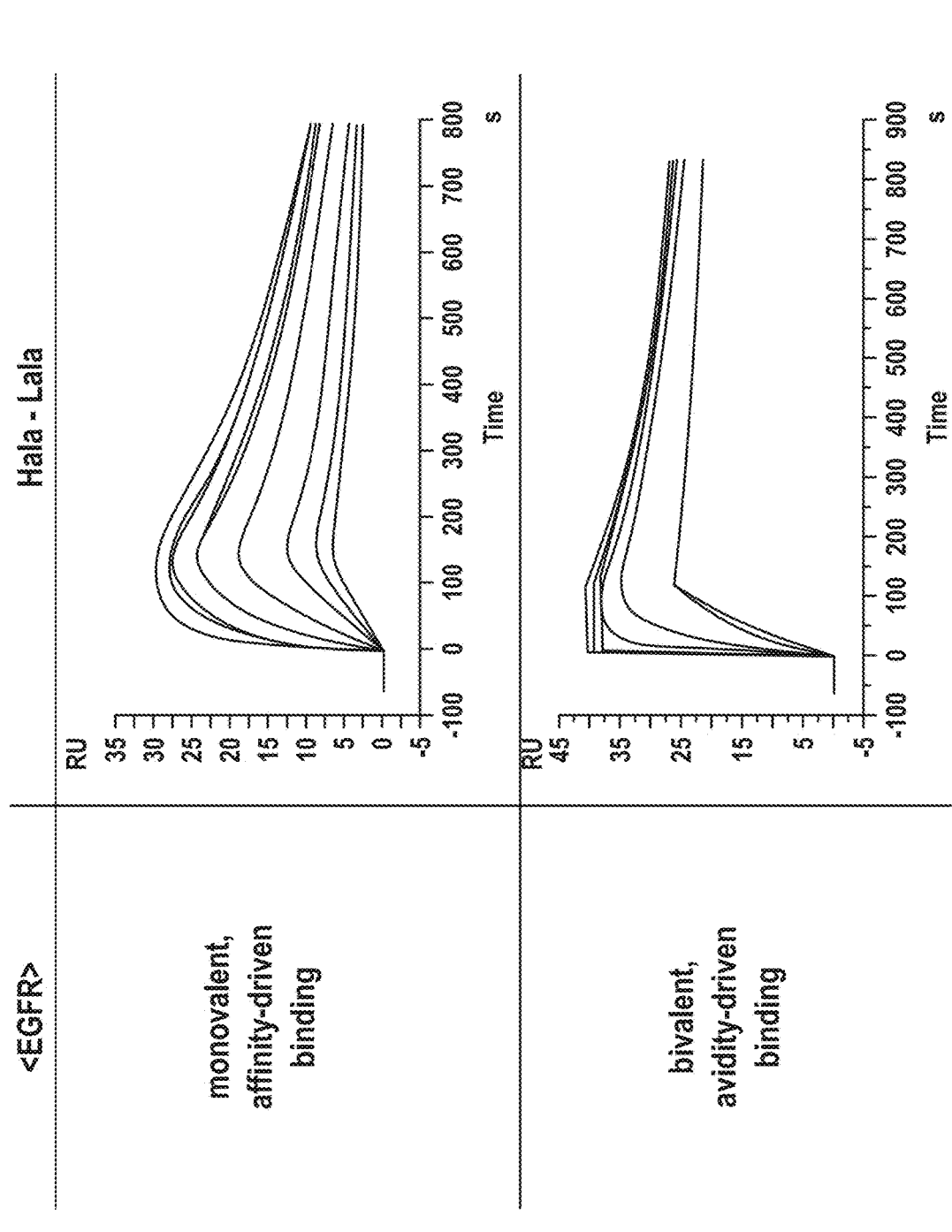
FIG. 26 A comparison of the binding characteristics of AlaR-derived anti-EGFR/Her1 antibody with the corresponding parent and invention-derived antibodies. Shown are SPR profiles based on affinity-mediated and avidity-mediated binding kinetics for the Hala-Lala combination.

Altschul, S. F., et al., 1990, J. Mol. Biol., 215: 403-10.

Berman, H. M., et al., 2000, Nucl. Acids Res., 28: 235-42.

Brinkmann, U., and R. E. Kontermann. 2017, MAbs, 9: 182-212.

Brochet, X., M. P. Lefranc, and V. Giudicelli, 2008, Nucl. Acids Res., 36: W503-8.

Bujotzek, A., et al., 2015, Proteins, 83: 681-95.

Bujotzek, A., et al., 2015, MAbs, 7: 838-52.

Chan, T. D., and R. Brink, 2012, Immunol. Rev., 247: 11-23.

Chuang, G. Y., et al., 2015, Prot. Sci., 24: 1019-30.

Dassault Systèmes BIOVIA, Discovery Studio 2017 R2, San Diego: Dassault Systèmes. In. 2016.

Demarest, S. J., et al., 2011, MAbs, 3: 338-51.

Dunbar, J., and C. M. Deane, 2016, Bioinformatics, 32: 298-300.

Dunbar, J., et al., 2014, Nucl. Acids Res., 42: D1140-6.

Fesnak, A., et al., 2016, Transfus. Med. Rev., 30: 139-45.

Finney, J., and G. Kelsoe, 2018, Retrovirology, 15: 53.

Foote, J., 2003, Science, 299: 1327-8.

Foote, J., and C. Milstein, 1994, Proc. Natl. Acad. Sci. USA, 91: 10370-4.

Garber, K, 2014, Nat. Rev. Drug Discov., 13: 799-801.

Giudicelli, V., et al., 2011, Cold Spring Harb Protoc, 2011: 695-715.

Grote, M., et al., 2012, Methods Mol. Biol., 901: 247-63.

Haurum, J. S., 2006, Drug Discov. Today, 11: 655-60.

Hongo, J. S., et al., Hybridoma 2000; 19:215-27.

Hudziak, R. M., et al., 1989, Mol. Cell. Biol., 9: 1165-72.

James, L. C., and D. S. Tawfik, 2005, Proc. Natl. Acad. Sci. USA, 102: 12730-5.

Johnson, G., and T. T. Wu, 2000, Nucl. Acids Res., 28: 214-8.

Kelly, R. L., et al., 2017, MAbs, 9: 1036-40.

Khandelwal, S., et al., 2018, Blood, 132: 2431-40.

Kollman, P. A., et al., 2000, Acc. Chem. Res., 33: 889-97.

Kontermann, R. E., 2012, MAbs, 4: 182-97.

Kortemme, T., et al., Sci. STKE 2004; 2004: p 12.

Kroon, G. J., et al., 2003, Prot. Sci., 12: 1386-94.

MacLennan, I. C., 1994, Ann. Rev. Immunol., 12: 117-39.

Manivel, V., et al., 2000, Immunity, 13: 611-20.

Mazor, Y., et al., 2017, Sci. Rep., 7: 40098.

Miller, B. J., et al., 1991, J. Autoimmun., 4: 665-79.

Mouquet, H., et al., 2010, Nature, 467: 591-5.

Niewoehner, J., et al., 2014, Neuron, 81: 49-60.

Pons, J., et al., 1999, Prot. Sci., 8: 958-68.

Schlothauer, T., et al., 2016, Prot. Eng. Des. Sel., 29: 457-66.

Tate, J., and G. Ward, 2004, Clin. Biochem. Rev., 25: 105-20.

Thorey, I. S., et al., 2016, Meth. Mol. Biol., 1364: 219-34.

Tiller, K. E., and P. M. Tessier, 2015, Ann. Rev. Biomed. Eng., 17: 191-216.

Vajdos, F. F., et al., J. Mol. Biol. 2002; 320:415-28.

van Spriel, A. B., et al., 2000, Immunol. Today, 21: 391-7.

Wang, W., et al., 2001, Ann. Rev. Biophys. Biomol. Struct., 30: 211-43.

Zhu, Z., et al., J. Virol. 2011; 85:11401-8.

EXAMPLES

Materials and Methods

All structural analysis is performed with BIOVIA Discovery Studio ("Dassault Systèmes BIOVIA, Discovery Studio 2017 R2, San Diego: Dassault Systèmes" 2016) and Pipeline Pilot ("Dassault Systèmes BIOVIA, Discovery Studio 2017 R2, San Diego: Dassault Systèmes" 2016).

Example 1

Expression and Purification

Amino acid sequences of monovalent IgG antibodies against hCD138, hHer2/c-neu, and hEGFR/Her1 were identified. These sequences were used as master to generate affinity variants. All antibodies were expressed transiently in non-adherent HEK-293 cells and purified using protein-A affinity and size-exclusion chromatography using an Äkta system (GE Healthcare) (Grote et al. 2012; Thorey et al. 2016). To verify antibody identity electrospray ionization mass spectra were acquired on a maXis Q-TOF (Bruker Daltonics, Bremen, Germany) equipped with a TriVersa NanoMate (Advion, Ithaca, NY).

| specificity | expression system | variant | Yield [mg/L] |
|---|---|---|---|
| CD138 | HEK293F | Hw-Lw (parent IgG) | 47 |
| | | Hw-La | 50 |
| | | Hw-Lg | 49 |
| | | Ha-Lw | 42 |
| | Expi293F | Ha-La | 216 |
| | | Ha-Lg | 220 |
| | HEK293F | Hb-Lw | 50 |
| | | Hb-La | 33 |
| | | Hb-Lg | 48 |
| | | Hg-Lw | 46 |
| | | Hg-La | 56 |
| | | Hg-Lg | 62 |
| Her2/c-neu | Expi293F | Hw-Lw (parent IgG) | 47 |
| | | Hw-La | 297 |
| | | Hw-Lb | 175 |
| | | Hw-Lg | 83 |
| | | Ha-Lw | 392 |
| | | Hb-Lw | 103 |
| | | Hg-Lw | 170 |
| | | Hg-Lg | 325 |
| EGFR/Her1 | HEK293F | Hw-Lw (parent IgG) | 23 |
| | | Hw-La | 50 |
| | | Hw-Lb | 38 |
| | | Hw-Lg | 72 |
| | | Ha-Lw | 22 |
| | | Hb-Lw | 23 |
| | | Hg-Lw | 22 |
| | | Hg-Lg | 46 |

None of the proteins behaved aberrantly and expression levels of affinity variants were comparable or higher as to their corresponding non-mutated WT IgG's. This indicates that the mutations introduced based on the method according to the invention are well tolerated and that there is no influence of individual or combined mutations on folding and antibody structure. There were no structural incompatibilities of H- and L-variants upon combination within the combination set and molecular mass was determined to be correct for each antibody.

| specificity | expression system | variant | yield in [mg/L] |
|---|---|---|---|
| CD138 | HEK293F | Hala-Lala | 114 |
| Her 2 | EXPI | Hala-Lala | 909 |
| EGFR/Her1 | HEK293F | Hala-Lala | 152 |

Example 2

Surface Plasmon Resonance to Determine Antibody Kinetics

The kinetics of all antibody affinity variants (anti-hCD138, anti-hHer2/c-neu, anti-hEGFR/Her1) to the extracellular matrix domain of the corresponding antigen was evaluated using a BIAcore T200 instrument (GE Healthcare)

(see Schlothauer et al. 2016). Association and dissociation were determined both, in a monovalent (affinity-driven) and bivalent (avidity-driven) binding mode.

CD138 Affinity SPR

Solution of anti-CD138 antibody affinity variants 30 nM in HBS-P+ (GE Healthcare) were captured with anti-huFc antibody (GE Healthcare BR-1008-39) on a CM5 sensor chip for 60 sec. (capture Level ~900 RU). Thereafter the interaction with hCD138 (R&D-S. 2780-TS) was analyzed in a dilution series of 66 nM to 600 nM using 150 sec. association time and 600 sec. dissociation time at a flow rate of 30 µl/min. All BIAcore T200 experiments were carried out in HBS-P+ (GE Healthcare) pH 7.4 running buffer and at 25° C. Binding curves were evaluated using T200 evaluation software and the for the calculation of binding properties 1:1 Langmuir binding model was used.

CD138 Avidity SPR

For the determination of avidity-driven binding kinetics to CD138 the antigen was immobilized to 240 response units (RU) on a CM5 chip using the amine coupling kit (GE Healthcare) at pH 4.5 and 1 µg/ml. Thereafter the interaction of CD138 on the CM5 surface and anti-CD138 antibody affinity variants was analyzed in a dilution series of 33 nM to 300 nM in HBS-P+ (GE Healthcare) using 120 sec. association time and 600 sec. dissociation time at a flow rate of 60 µl/min. The surface regeneration was performed by a 60 sec. washing step with a 3 M MgCl$_2$. All BIAcore T200 experiments were carried out in HBS-P+ (GE Healthcare) pH 7.4 running buffer and at 25° C. Binding curves were evaluated using BIAcore T200 evaluation software and for the calculation of binding properties 1:1 Langmuir binding model was used. Further analysis of heterogonous interaction was performed using Interaction Map software (Ridgeview Instruments AB).

Her2/c-neu Affinity SPR

The anti-Her2/c-neu antibody affinity variants at 5 nM in HBS-P+ (GE Healthcare) were captured with anti-huFc antibody (GE Healthcare BR-1008-39) on a CM5 sensor chip for 30 sec. (capture Level ~100 RU). Thereafter hHer2/c-neu ECD was injected at a concentration of 19 nM to 300 nM diluted in HBS-P+ (GE Healthcare) with 150 sec. association time and 720 sec. dissociation time. All BIAcore T200 experiments were carried out in HBS-P+ (GE Healthcare) pH 7.4 running buffer and at 25° C. Binding curves were evaluated using T200 evaluation software and the for the calculation of binding properties 1:1 Langmuir binding model was used.

Her2/c-neu Avidity SPR

For the determination of avidity-driven binding kinetics the hHer2/c-neu ECD was immobilized to 60 response units (RU) on a CM5 chip using the amine coupling kit (GE Healthcare) at pH 4.5 and 1 µl/min. Thereafter the interaction of hHer2/c-neu ECD on the surface and anti-hHer2/c-neu antibody variants was analyzed in a dilution series from 7 nM to 600 nM in HBS-P+ (GE Healthcare) using 150 sec. association time and 600 sec. dissociation time at a flow rate of 60 µl/min followed by regeneration of the surface by a 60 sec. washing step with 3 M MgCl$_2$. All BIAcore T200 experiments were carried out in HBS-P+ (GE Healthcare) pH 7.4 running buffer and at 25° C. Binding curves were evaluated using BIAcore T200 evaluation software and for the calculation of binding properties 1:1 Langmuir binding model was used.

EGFR/Her1 Affinity SPR

The anti-EGFR/Her1 antibody affinity variants at 5 nM in HBS-P+ (GE Healthcare) were captured with anti-huFc antibody (GE Healthcare BR-1008-39) on a CM5 sensor chip for 30 sec. (capture Level ~100 RU). Thereafter the interaction with hEGFR/Her1 ECD antigen was analyzed in a dilution series from 19 nM to 300 nM using 120 sec. association time and 600 sec. dissociation time at a flow rate of 60 µl/min. All BIAcore T200 experiments were carried out in HBS-P+ (GE Healthcare) pH 7.4 running buffer and at 25° C. Binding curves were evaluated using BIAcore T200 evaluation software and for the calculation of binding properties 1:1 Langmuir binding model was used.

EGFR/Her1 Avidity SPR

An SA-chip was coated with ~200 response units (RU) of hEGFR/Her1 ECD antigen. Binding kinetics were determined using a dilution series from 1.1 nM to 90 nM anti-hEGFR/Her1 antibodies in HBS-P+ (GE Healthcare) and a flow rate of 60 µl/min with 120 sec. association time and 600 sec. dissociation time. The surface regeneration was performed by a 30 sec. injection of 10 mM NaOH. All BIAcore T200 experiments were carried out in HBS-P+ (GE Healthcare) pH 7.4 running buffer and at 25° C. Binding curves were evaluated using BIAcore T200 evaluation software and for the calculation of binding properties 1:1 Langmuir binding model was used. Further analysis of heterogonous interaction was performed using Interaction Map software (Ridgeview Instruments AB).

In the following Table are listed on-rates ($k_a$) and off-rates ($k_d$) as well as $K_D$-values of antibodies and corresponding variants measured in a monovalent assay set up.

'no valid signal': very small 'on' signals were observed for some CD138 binders which may point towards weak interactions, which however cannot be called true binding events based on these monovalent SPR analyses.

| specificity | VH-VL combination | $k_a$ [1/Ms] | $k_d$ [1/s] | $K_D$ [M] |
|---|---|---|---|---|
| CD138 | Hw-Lw (parent IgG) | 7.7E+04 | 6.2E−03 | 8.0E−08 |
| | Hw-La | 8.7E+04 | 6.1E−03 | 7.1E−08 |
| | Hw-Lg | 1.3E+04 | 2.5E−02 | 2.0E−07 |
| | Ha-Lw | 7.6E+04 | 1.5E−02 | 1.9E−07 |
| | Ha-La | 5.5E+04 | 1.3E−02 | 2.4E−07 |
| | Ha-Lg | 1.2E+05 | 4.5E−02 | 3.8E−07 |
| | Hb-Lw | 1.8E+05 | 2.7E−02 | 1.5E−07 |
| | Hb-La | 1.7E+05 | 2.5E−02 | 1.4E−07 |
| | Hb-Lg | 1.3E+05 | 7.9E−02 | 6.1E−07 |
| | Hg-Lw | No valid result | No valid result | No valid result |
| | Hg-La | No valid result | No valid result | No valid result |
| | Hg-Lg | No valid result | No valid result | No valid result |
| Her2/c-neu | Hw-Lw (parent IgG) | 1.5E+05 | 2.8E−04 | 1.9E−09 |
| | Hw-La | 1.3E+05 | 2.5E−04 | 1.9E−09 |
| | Hw-Lb | 1.5E+05 | 4.1E−04 | 2.7E−09 |
| | Hw-Lg | 1.4E+05 | 2.6E−04 | 1.9E−09 |
| | Ha-Lw | 1.5E+05 | 3.1E−04 | 2.1E−09 |
| | Hb-Lw | 4.1E+04 | 1.6E−02 | 3.9E−07 |
| | Hg-Lw | 6.5E+04 | 2.2E−02 | 3.4E−07 |
| | Hg-Lg | 6.1E+04 | 2.4E−02 | 3.9E−07 |
| EGFR/Her1 | Hw-Lw (parent IgG) | 1.07E+06 | 6.4E−04 | 6.0E−10 |
| | Hw-La | 9.97E+05 | 3.5E−03 | 3.5E−09 |
| | Hw-Lb | 8.90E+05 | 3.5E−03 | 3.9E−09 |
| | Hw-Lg | 1.00E+06 | 8.5E−03 | 8.5E−09 |
| | Ha-Lw | 1.06E+06 | 8.0E−04 | 7.3E−10 |
| | Hb-Lw | 1.06E+06 | 7.0E−04 | 6.6E−10 |
| | Hg-Lw | 1.13E+06 | 1.1E−03 | 9.7E−10 |
| | Hg-Lg | 1.08E+06 | 1.3E−02 | 1.2E−08 |

In the following Table are listed on- and off-rates as well as $K_D$-values of antibodies and corresponding variants measured in a bivalent assay set up.

'no valid result': very small 'on' signals were observed for some CD138 binders which may point towards weak interactions, which however cannot be called true binding events based on these monovalent SPR analyses.

| specificity | VH-VL combination | $k_a$ [1/Ms] | $k_d$ [1/s] | $K_D$ [M] |
|---|---|---|---|---|
| CD138 | Hw-Lw (parent IgG) | 3.3E+05 | 7.8E−05 | 2.4E−10 |
| | Hw-La | 3.6E+05 | 8.7E−05 | 2.4E−10 |
| | Hw-Lg | 3.6E+05 | 1.3E−04 | 3.6E−10 |
| | Ha-Lw | 1.7E+05 | 7.1E−05 | 4.2E−10 |
| | Ha-La | 1.6E+05 | 6.4E−05 | 4.0E−10 |
| | Ha-Lg | 1.6E+05 | 2.9E−04 | 8.3E−10 |
| | Hb-Lw | 3.5E+05 | 1.1E−04 | 2.8E−10 |
| | Hb-La | 4.0E+05 | 1.2E−04 | 3.1E−10 |
| | Hb-Lg | 3.9E+05 | 5.0E−04 | 2.4E−09 |
| | Hg-Lw | 2.1E+05 | 5.1E−02 | 2.3E−07 |
| | Hg-La | 2.2E+05 | 3.8E−02 | 1.7E−07 |
| | Hg-Lg | No valid result | No valid result | No valid result |
| Her2/c-neu | Hw-Lw (parent IgG) | 1.6E+05 | 7.0E−05 | 4.4E−10 |
| | Hw-La | 2.6E+05 | 7.1E−05 | 2.7E−10 |
| | Hw-Lb | 1.7E+05 | 1.7E−04 | 1.0E−09 |
| | Hw-Lg | 8.2E+05 | 1.3E−04 | 1.6E−10 |
| | Ha-Lw | 1.6E+05 | 7.1E−05 | 4.4E−10 |
| | Hb-Lw | 3.1E+04 | 2.1E−04 | 6.8E−09 |
| | Hg-Lw | 8.7E+04 | 1.5E−02 | 1.7E−07 |
| | Hg-Lg | 8.3E+04 | 1.5E−02 | 1.8E−07 |
| EGFR/Her1 | Hw-Lw (parent IgG) | 1.5E+5 | 9.4E−05 | 6.3E−10 |
| | Hw-La | 1.6E+5 | 1.3E−04 | 8.1E−10 |
| | Hw-Lb | 1.5E+5 | 1.2E−04 | 8.0E−10 |
| | Hw-Lg | 1.4E+5 | 1.4E−04 | 1.0E−10 |
| | Ha-Lw | 1.5E+5 | 1.0E−04 | 6.7E−11 |
| | Hb-Lw | 4.1E+4 | 9.3E−05 | 2.3E−10 |
| | Hg-Lw | 6.5E+4 | 1.1E−04 | 1.7E−09 |
| | Hg-Lg | 6.1E+4 | 1.7E−04 | 2.8E−08 |

Example 3

Polyreactivity Assays

ELISA based polyreactivity assays were performed using non-specific antigens and specific antigens as positive controls. The antigens were coated to 384-well Nunc-Maxi Sorp plates at concentrations between 0.1 and 2 µg/mL in PBS at 4° C. over night. Between individual steps plates were washed with PBST (1×PBS+0.1% Tween 20). Blocking was performed (2% BSA in PBS+0.2% Tween 20) for 1 hour at room temperature without agitation. Antibody samples (1 µg/mL in One Step ELISA buffer; 1×PBS+0.5% BSA+ 0.05% Tween 20) were incubated 1 hour at room temperature without agitation. Secondary antibody (anti-human IgG Fc-specific; Jackson #109-036-098; dilution 1:7000 in OSEP) was added and incubated for 1 hour at room temperature on a microplate shaker at 400 rpm. Detection substrate TMB was added (4 Min without agitation) and absorbance was measured at a wavelength of 370 nm and a reference wavelength at 492 nm using a Tecan Safire II ELISA reader. The raw measurement signals at 492 nm were subtracted from the respective raw measurement signals at 370 nm (absorbance correction). The absorbance corrected signals from the blank wells (secondary antibody only) were subtracted from the absorbance corrected signals on the respective antigens (Blank correction). All measurements were done in triplicates.

The invention claimed is:

1. A method for decreasing the binding affinity of a bispecific antibody comprising a first binding site specifically binding to a first cell-surface antigen and a second binding site specifically binding to a second cell-surface antigen, with said first and second antigen being on the same cell, wherein the first binding site is a mammalian or mammalianized binding site, wherein the first binding site is at least a pair of an immunoglobulin light chain variable domain and an immunoglobulin heavy chain variable domain, wherein the decreasing the binding affinity is a decreasing of the binding affinity of the first binding site to its antigen by mutating in the first binding site at least one amino acid residue at a position in the CDRs of the light chain variable domain or in the CDR1 or CDR2 of the heavy chain variable domain or in the two framework positions directly preceding the CDR3 in the heavy chain variable domain to an amino acid residue present at said position in a germline variable domain immunoglobulin amino acid sequence of the same mammalian species as that of the mammalian or mammalianized binding site, wherein the germline variable domain immunoglobulin amino acid sequence has the highest identity of all germline variable domain immunoglobulin amino acid sequences of the mammalian species to the respective light or heavy chain variable domain of the first binding site of the bispecific antibody, based on a sequence alignment of said all germline variable domain immunoglobulin amino acid sequences of the mammalian species to the respective light or heavy chain variable domain of the first binding site of the bispecific antibody, and wherein the mutated mammalian or mammalianized binding site is free of polyreactivity.

2. The method according to claim 1, wherein the germline variable domain immunoglobulin amino acid sequence is a germline heavy chain variable domain immunoglobulin amino acid sequence, wherein the germline variable domain immunoglobulin amino acid sequence has the highest identity of all germline heavy chain variable domain immunoglobulin amino acid sequences of the mammalian species to the heavy chain variable domain of the first binding site of the bispecific antibody, based on a sequence alignment of all germline heavy chain variable domain immunoglobulin amino acid sequences to the respective heavy chain variable domain sequence of the first binding site of the bispecific antibody, and wherein the heavy chain variable domain sequences used for the alignment span the first residue of CDR1 of the heavy chain variable domain to the last residue of the CDR2 of the heavy chain variable domain.

3. The method according to claim 1 or 2, wherein the side-chains of the amino acid residues to be mutated are solvent accessible.

4. The method according to claim 1 or 2, wherein the side-chains of the amino acid residues to be mutated are not involved in a VH-VL interactions.

5. The method according to claim 1 or 2, wherein the side-chains of the amino acid residues to be mutated are involved in interactions with the antigen.

6. The method according to claim 1 or 2, wherein the method further comprises mutating at least one amino acid residue in the second mammalian or mammalianized binding site, wherein the second binding site is at least a second pair of an immunoglobulin light chain variable domain and an immunoglobulin heavy chain variable domain, or the second binding site is a second mammalian or mammalianized binding site and the mutating is of at least one amino acid residue in the first and the second mammalian, or mammalianized binding site.

7. The method according to claim 1 or 2, wherein the mammal is a human.

\* \* \* \* \*